US007723391B2

(12) United States Patent
Du Bois et al.

(10) Patent No.: US 7,723,391 B2
(45) Date of Patent: May 25, 2010

(54) CYCLOPROPYL ARYL AMIDE DERIVATIVES AND USES THEREOF

(75) Inventors: Daisy Joe Du Bois, Palo Alto, CA (US); David Garrett Loughhead, Belmont, CA (US); Hans Maag, Sausalito, CA (US); Jason Manka, Sunnyvale, CA (US); David Bernard Smith, San Mateo, CA (US); David Nigel Hurst, Welwyn (GB)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 12/286,842

(22) Filed: Oct. 2, 2008

(65) Prior Publication Data

US 2009/0093525 A1 Apr. 9, 2009

Related U.S. Application Data

(60) Provisional application No. 60/997,581, filed on Oct. 4, 2007.

(51) Int. Cl.
*A61K 31/166* (2006.01)
*C07C 233/64* (2006.01)

(52) U.S. Cl. .................. 514/617; 514/622; 564/161; 564/176

(58) Field of Classification Search .................. 564/86, 564/176; 514/603, 622
See application file for complete search history.

(56) References Cited

U.S. PATENT DOCUMENTS

| 3,192,229 A | 6/1965 | Biel et al. |
| 4,694,016 A | 9/1987 | Lu et al. |
| 5,750,549 A | 5/1998 | Caldwell et al. |
| 2003/0191279 A1 | 10/2003 | Goldstein et al. |
| 2004/0127536 A1 | 7/2004 | Bhagwat et al. |
| 2005/0009876 A1 | 1/2005 | Bhagwat et al. |
| 2007/0167497 A1 | 7/2007 | Nambu et al. |

FOREIGN PATENT DOCUMENTS

| EP | 0 284 174 B1 | 7/1992 |
| EP | 1 388 535 A1 | 2/2004 |
| EP | 1 088 819 B1 | 6/2005 |
| WO | WO 99/05111 A1 | 2/1999 |
| WO | WO 99/05115 A1 | 2/1999 |
| WO | WO 99/27783 A1 | 6/1999 |
| WO | WO 00/42017 A1 | 7/2000 |
| WO | WO 00/42018 A1 | 7/2000 |
| WO | WO 00/42020 A1 | 7/2000 |
| WO | WO 00/42034 A1 | 7/2000 |
| WO | WO 01/44213 A1 | 6/2001 |
| WO | WO 01/51470 A1 | 7/2001 |
| WO | WO 02/05616 A1 | 1/2002 |
| WO | WO 02/06238 A1 | 1/2002 |
| WO | WO 02/06239 A1 | 1/2002 |
| WO | WO 02/072090 A1 | 9/2002 |
| WO | WO 03/018536 A1 | 3/2003 |
| WO | WO 2004/009610 A2 | 1/2004 |
| WO | WO 2004/009610 A3 | 1/2004 |
| WO | WO 2004/018431 A2 | 3/2004 |
| WO | WO 2004/018431 A3 | 3/2004 |
| WO | WO 2004/019944 A1 | 3/2004 |
| WO | WO 2004/081011 A1 | 9/2004 |
| WO | WO 2004/093799 A2 | 11/2004 |
| WO | WO 2004/093799 A3 | 11/2004 |
| WO | WO 2005/012252 A1 | 2/2005 |
| WO | WO 2005/012253 | 2/2005 |
| WO | WO 2005/077906 A1 | 8/2005 |
| WO | WO 2005/085203 A1 | 9/2005 |
| WO | WO 2005/087744 A1 | 9/2005 |
| WO | WO 2005/087745 A1 | 9/2005 |
| WO | WO 2005/090311 A1 | 9/2005 |
| WO | WO 2007/039173 A1 | 4/2007 |
| WO | WO 2007/134799 A1 | 11/2007 |

OTHER PUBLICATIONS

Wolf et al., Enantioseparations by electrochematography with packed capillaries, 1997, Journal of Chromatography A., 782, pp. 175-179.*

Bondon, A., et. al. "Oxidation of Cycloalkylamines by Cytochrome P-450," *The Journal of Biological Chemistry*, 1989, vol. 264 (4), pp. 1988-1997.

Vlaeminck, F. et. al. "Benzo- and Indoloquinolizidines. Part XVIII. The Preparation of 4b,5,6,7,7°,9,10,14b-Octahydrodibenzo[a,h]Cyclopenta [c] Quinolizine Isomers. An Application of Stereoselective Iminium Cyclisations." *Heterocycles* 1979, vol. 12 (3), pp. 329-335.

Brown, R. S., et. al. "Substituent Effects on σ- Conjugation. The Absence of Electron Transmission through Cyclopropane Rings[1,2]" *J. American Chemical Soc.* 1973, pp. 8025-8032.

(Continued)

*Primary Examiner*—Kamal A Saeed
*Assistant Examiner*—Kristin Bianchi
(74) *Attorney, Agent, or Firm*—Robert C. Hall

(57) ABSTRACT

Compounds of the formula:

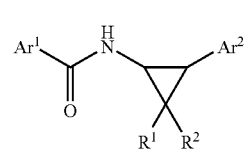

wherein $Ar^1$, $Ar^2$, $R^1$ and $R^2$ are as defined herein. Also provided are pharmaceutical compositions, methods of using, and methods of preparing the subject compounds.

18 Claims, No Drawings

OTHER PUBLICATIONS

Burger, A., et. al. "Arylcyloalkylamines. I. 2-Phenylcyclopropylamine," *J. American Chemical Soc.* 1948, vol. 70, pp. 2198-2201.

White, W. L., et. al. New Reactions of Polyfluoroaromatic Compounds. Part II. † Polyfluoroaralkyl Amines[1] *J. American Chemical Soc.* 1971, pp. 2062-2068.

* cited by examiner under CYCLOPROPYL ARYL AMIDE DERIVATIVES AND USES THEREOF

CROSS REFERENCE TO RELATED APPLICATIONS

This application claims the benefit of priority of U.S. Provisional Patent Application Ser. No. 60/997,581, filed Oct. 4, 2007, the disclosure of which is incorporated herein by reference in its entirety.

FIELD OF THE INVENTION

This invention relates to nicotinic acetylcholine receptor ligands (nAChR), and particularly to positive allosteric modulators for the α7 nAChR subtype, and methods of making and using such compounds.

BACKGROUND OF THE INVENTION

Nicotinic acetylcholine receptors (nAChR) are members of the ligand-gated ion channel family. When activated, the conductance of ions across the nicotinic ion channels increases. Nicotinic alpha 7 receptor (alpha 7 nAChR) forms a homopentameric channel in vitro that is highly permeable to calcium cations. Each alpha 7 nAChR has four transmembrane domains, known as M1, M2, M3, and M4. The M2 domain has been suggested to form the wall lining the channel. Sequence alignment shows that the alpha 7 nAChR is highly conserved during evolution. The M2 domain that lines the channel is identical in protein sequence from chick to human. Alpha 7 nAChR is described by, Revah et al. (1991), *Nature,* 353, 846-849; Galzi et al. (1992), *Nature* 359, 500-505; Fucile et al. (2000), *PNAS* 97(7), 3643-3648; Briggs et al. (1999), *Eur. J. Pharmacol.* 366 (2-3), 301-308; and Gopalakrishnan et al. (1995), *Eur. J. Pharmacol.* 290(3), 237-246.

The alpha 7 nAChR channel is expressed in various brain regions and is believed to be involved in many important biological processes in the central nervous system (CNS), including learning, memory and attention (Levin et al., *Psychopharmacology* (1998), 138, 217-230). Alpha 7 nAChR are localized on both presynaptic and postsynaptic terminals and have been suggested to be involved in modulating synaptic transmission. Agonists of alpha 7 nAChR have been shown to improve attention and cognition in Alzheimer's and attention deficit disorder conditions (Wilens et al., *Am. J. Psychiatry* (1999), 156(12), 1931-1937).

The analgesic effects of nicotine have long been known. Agonists of the alpha 7 nAChR receptor have been shown to modulate production of pro-inflammatory cytokines, including interleukins (ILs), tumor necrosis factor (TNF) alpha, and high-mobility group box (HMGB-1), and to inhibit inflammatory signalling in the CNS (de Jonge et al., *Br. J. Pharmacol.* (2007), 1-15). The alpha 7 nAChR receptor has a role in modulating CNS pain transmission, and alpha 7 nAChR agonists have shown an antinociceptive effect in an acute pain model (Damaj et al., *Neuropharmacol.*(2000) 39, 2785-2791.

Since acetylcholine (ACh) is an endogenous agonist of alpha 7 nAChR, agonists that act at the same site as ACh can stimulate and possibly block receptor activity through desensitization and competitive blockade processes (Forman et al., *Biophysical J.*(1988), 54(1), 149-158) and lead to prolonged receptor inactivation (Buisson et al., *J. Neurosci.*(2001), 21(6), 1819-1829). Desensitization limits the duration that the ion channel remains activated during agonist application. Thus the enhancement of Alpha 7 nAChR activity provided by such agonists will also increase competition with ACh, and therefore limit the usefulness of agonists as drugs.

Positive allosteric modulators of the nicotinic alpha 7 receptor channel enhance the activity of ACh and other nicotinic alpha 7 receptor agonists. Positive allosteric modulators activate alpha 7 nAChR when sufficient ACh is present in the central nervous system. Positive allosteric modulators of alpha 7 nAChRs thus are useful for treatment of CNS, pain and inflammatory diseases or conditions, to regulate CNS functions such as cognition, learning, mood, emotion and attention, and control production of pro-inflammatory cytokines associated with pain and inflammatory conditions. There is accordingly a need for new positive allosteric modulators of the nicotinic alpha 7 receptor channel.

SUMMARY OF THE INVENTION

One aspect of the invention provides compounds of formula I:

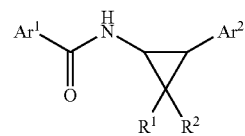

or a pharmaceutically acceptable salt thereof,
wherein:
  $Ar^1$ and Ar2 each independently is:
    optionally substituted aryl; or
    optionally substituted heteroaryl; and
  $R^1$ and $R^2$ each independently is:
    hydrogen;
    fluoro;
    $C_{1-6}$alkyl; or
    halo-$C_{1-6}$alkyl.

The invention also provides pharmaceutical compositions and methods of using the aforementioned compounds.

In another aspect of the invention there is provided a method for preparing a compound of formula r

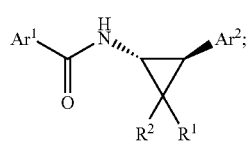

wherein $Ar^1$, $Ar^2$, $R^1$ and $R^2$ are as defined herein, the method comprising:
  reacting a cinnamate compound of formula s

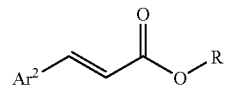

with a Wittig reagent of formula t

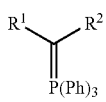

to form a cyclopropylester compound of formula u

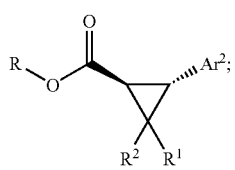

hydrolyzing the cyclopropyl ester compound of formula u to afford a cyclopropyl acid compound of formula p

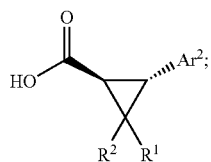

treating the cyclopropyl acid compound of formula p with chloroformate ester, followed by sodium azide and acidification, to afford a cyclopropyl amine compound of formula q

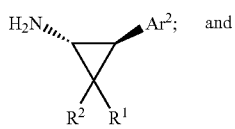

reacting the cyclopropyl amine compound of formula q with an acyl reagent of formula i

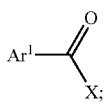

wherein X is hydroxy, halo or alkoxy, to form the compound of formula r.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like. "Branched alkyl" means isopropyl, isobutyl, tert-butyl, "Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, tert-butoxy and the like.

"Alkoxyalkyl" means a moiety of the formula —R'—R", where R' is alkylene and R" is alkoxy as defined herein. Exemplary alkoxyalkyl groups include, by way of example, 2-methoxypropyl, 3-methoxypropyl, 1-methyl-2-methoxyethyl, 1-(2-methoxyethyl)-3-methoxypropyl, and 1-(2-methoxyethyl)-3-methoxypropyl.

"Alkylcarbonyl" means a moiety of the formula —C(O)—R, where R' is alkyl as defined herein.

"Alkylsulfonyl" means a moiety of the formula —$SO_2$—R' where R' is alkyl as defined herein.

"Amino" means a moiety of the formula —NRR' where R and R' each independently is hydrogen or alkyl as defined herein.

"Aminosulfonyl" means a moiety of the formula —$SO_2$—R' where R' is amino as defined herein.

"Alkylsulfonylalkyl" means a moiety of the formula —$R^b$—$SO_2$—$R^a$, where $R^a$ is alkyl and $R^b$ is alkylene as defined herein. Exemplary alkylsulfonylalkyl groups include, by way of example, 3-methanesulfonylpropyl, 2-methanesulfonylethyl, 2-methanesulfonylpropyl, and the like.

"Alkylsulfonyloxy" means a moiety of the formula $R^a$—$SO_2$—O—, where $R^a$ is alkyl as defined herein.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof, each of which may be optionally substituted. A preferred aryl is optionally substituted phenyl.

"Aryloxy" means a moiety of the formula —OR, wherein R is an aryl moiety as defined herein.

"Arylalkyl" and "Aralkyl", which may be used interchangeably, mean a radical-$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Aralkoxy" means a moiety of the formula —OR, wherein R is an aralkyl moiety as defined herein.

"Cyanoalkyl" means a moiety of the formula —R'—R", where R' is alkylene as defined herein and R" is cyano or nitrile.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkyloxy" and "cycloalkoxy", which may be used interchangeably, mean a group of the formula —OR wherein R is cycloalkyl as defined herein. Exemplary cycloalkyloxy include cyclopropyloxy, cyclobutyloxy, cyclopentyloxy, cyclohexyloxy and the like.

"Cycloalkylalkyl" means a moiety of the formula —R'—R", where R' is alkylene and R" is cycloalkyl as defined herein.

"Cycloalkylalkyloxy" and "cycloalkylalkoxy", which may be used interchangeably, mean a group of the formula —OR wherein R is cycloalkylalkyl as defined herein. Exemplary cycloalkyloxy include cyclopropylmethoxy, cyclobutylmethoxy, cyclopentylmethoxy, cyclohexylmethoxy and the like.

"Heteroalkyl" means an alkyl radical as defined herein, including a branched $C_4$-$C_7$-alkyl, wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic, bicyclic or tricyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, imidazolyl, oxazolyl, isoxazolyl, thiazolyl, isothiazolyl, oxadiazolyl, thiadiazolyl, pyrazinyl, thienyl, thiophenyl, furanyl, pyranyl, pyridinyl, pyrrolyl, pyrazolyl, pyrimidyl, quinolinyl, isoquinolinyl, benzofuryl, benzofuranyl, benzothiophenyl, benzothiopyranyl, benzimidazolyl, benzoxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof, each of which may be optionally substituted. Preferred heteroaryl include indolyl, pyridinyl, pyrimidinyl, thienyl, furanyl pyrrolyl, imidazolyl and pyrazolyl, each of which may be optionally substituted.

"Heteroarylalkyl" and "heteroaralkyl", which may be used interchangeably, mean a radical-$R^aR^b$ where $R^a$ is an alkylene group and $R^b$ is a heteroaryl group as defined herein The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Haloalkoxy" means a moiety of the formula —OR, wherein R is a haloalkyl moiety as defined herein. Examples of haloalkoxy moieties include, but are not limited to, trifluoromethoxy, difluoromethoxy, 2,2,2-trifluoroethoxy, and the like.

"Hydroxyalkyl" refers to a subset of heteroalkyl and refers in particular to an alkyl moiety as defined herein that is substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Optionally substituted", when used in association with "aryl", phenyl", "heteroaryl" (including indolyl such as indol-1-yl, indol-2-yl and indol-3-yl, 2,3-dihydroindolyl such as 2,3-dihydroindol-1-yl, 2,3-dihydroindol-2-yl and 2,3-dihydroindol-3-yl, indazolyl such as indazol-1-yl, indazol-2-yl and indazol-3-yl, benzimidazolyl such as benzimidazol-1-yl and benzimidazol-2-yl, benzofuranyl such as benzofuran-2-yl and benzofuran-3-yl, benzothiophenyl such as benzothiophen-2-yl and benzothiophen-3-yl, benzoxazol-2-yl, benzothiazol-2-yl, thienyl, furanyl, pyridinyl, pyrimidinyl, pyridazinyl, pyrazinyl, oxazolyl, thiazolyl, isoxazolyl, isothiazolyl, imidazolyl, pyrazolyl and quinolinyl)" or "heterocyclyl", means an aryl, phenyl, heteroaryl or heterocyclyl which is optionally substituted independently with one to four substituents, preferably one or two substituents selected from alkyl, cycloalkyl, alkoxy, halo, haloalkyl, haloalkoxy, cyano, nitro, heteroalkyl, amino, mono-alkylamino, di-alkylamino, hydroxyalkyl, alkoxyalkyl, alkylsulfonyl, alkylsulfonamido, benzyloxy, cycloalkylalkyl, cycloalkoxy, cycloalkylalkoxy, alkylsulfonyloxy, optionally substituted thienyl, optionally substituted pyrazolyl, optionally substituted pyridinyl, morpholinocarbonyl, —(CH$_2$)$_q$—S(O)$_r$R$^f$; —(CH$_2$)$_q$—NR$^g$R$^h$; —(CH$_2$)$_q$—C(=O)—NR$^g$R$^h$; —(CH$_2$)$_q$—C(=O)—C(=O)—NR$^g$R$^h$; —(CH$_2$)$_q$—SO$_2$—NR$^g$R$^h$; —(CH$_2$)$_q$—N(R$^f$)—C(=O)—R$^i$; —(CH$_2$)$_q$—C(=O)—R$^i$; or —(CH$_2$)$_q$—N(R$^f$)—SO$_2$—R$^g$; where q is 0 or 1, r is from 0 to 2, R$^f$, R$^g$, and R$^h$ each independently is hydrogen or alkyl, and each R$^i$ is independently hydrogen, alkyl, hydroxy, or alkoxy. Certain preferred optional substituents for "aryl", phenyl", "heteroaryl" "cycloalkyl" or "heterocyclyl" include alkyl, halo, haloalkyl, alkoxy, cyano, amino, aminosulfonyl, and alkylsulfonyl. More preferred substituents are methyl, fluoro, chloro, trifluoromethyl, methoxy, amino, aminosulfonyl and methanesulfonyl.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Skilled persons will know how to choose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as H$_2$O, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Pain" and pain conditions (states) as used herein means pain associated with any of a wide variety of causes, including but not limited to, inflammatory pain, surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

"Inflammation" means any pathological process characterized by injury or destruction of tissues resulting from cytologic reactions, chemical reactions or other causes. Inflammation may be manifested by signs of pain, heat, redness, swelling, and loss of function. Inflammation indications include, but are not limited to, bacterial, fungal or viral infections, rheumatoid arthritis, osteoarthritis, surgery, bladder infection or idiopathic bladder inflammation, over-use, old age, or nutritional deficiencies, prostatis and conjunctivitis.

"Cognition" means any mental process associated with acquiring and retaining knowledge. A "cognition disorder" means any disturbance to the mental process or processes related to thinking, reasoning, judgment ad memory. Cognition disorders may result from or other wise be associated with Parkinson's disease, Huntington's disease, anxiety, depression, manic depression, psychosis, epilepsy, obsessive compulsive disorders, mood disorders, migraine, Alzheimer's disease, sleep disorders, feeding disorders such as anorexia, bulimia, and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen, sulfur or nitrogen atom in the structures herein indicates the presence of a hydrogen atom.

Whenever a chiral carbon is present in a chemical structure, it is intended that all stereoisomers associated with that chiral carbon are encompassed by the structure.

All patents and publications identified herein are incorporated herein by reference in their entirety.

Compounds of the Invention

The invention provides compounds of formula I:

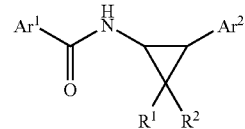

I or a pharmaceutically acceptable salt thereof, wherein:
$Ar^1$ and $Ar^2$ each independently is:
optionally substituted aryl; or
optionally substituted heteroaryl; and
$R^1$ and $R^2$ each independently is:
hydrogen;
fluoro;
$C_{1-6}$alkyl; or
halo-$C_{1-6}$alkyl.

In certain embodiments the compounds of the invention may be of formula Ia or Ib:

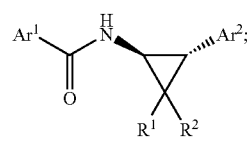

Ia

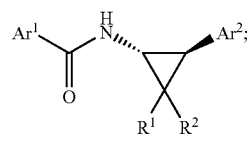

Ib wherein $Ar^1$, $Ar^2$, $R^1$ and $R^2$ are as defined herein.

In certain embodiments of formula I, Ia or Ib, $R^1$ and $R^2$ are $C_{1-6}$alkyl.

In certain embodiments of formula I, Ia or Ib, $Ar^1$ and $Ar^2$ are optionally substituted phenyl.

In certain embodiments of formula I, Ia or Ib, $Ar^1$ and $A^2$ are phenyl, each of which is optionally substituted with one, two or three groups each independently selected from:
$C_{1-6}$alkyl;
halo;
$C_{1-6}$alkoxy;
halo-$C_{1-6}$alkoxy;
halo-$C_{1-6}$alkyl;
hetero-$C_{1-6}$alkyl;
cyano;
$C_{1-6}$alkyl-amino;
di-$C_{1-6}$alkyl-amino;
nitro; or
—$(CR^aR^b)_m$—X—$R^3$ wherein:
X is C(O) or S(O)$_n$;
m is 0 or 1;
n is 0, 1 or 2;
$R^a$ and $R^b$ each independently is:
hydrogen; or
$C_{1-6}$alkyl; and R³ is:
hydrogen;
$C_{1-6}$alkyl;
$C_{1-6}$alkoxy;
hetero-$C_{1-6}$alkyl;
halo-$C_{1-6}$alkyl;
$C_{3-7}$cycloalkyl;
aryl;
heteroaryl;
heterocyclyl;
$C_{3-7}$cycloalkyl-$C_{1-6}$alkyl;
aryl-$C_{1-6}$alkyl;
heteroaryl-$C_{1-6}$alkyl;
heterocyclyl-$C_{1-6}$alkyl;
$C_{3-7}$cycloalkyloxy;
aryloxy;
heteroaryloxy;
heterocyclyloxy;
$C_{3-7}$cycloalkyloxy-$C_{1-6}$alkyl;
aryloxy-$C_{1-6}$alkyl;
heteroaryloxy-$C_{1-6}$alkyl;
heterocyclyloxy-$C_{1-6}$alkyl; or
—NR⁴R⁵, wherein:
R⁴ is:
hydrogen; or
$C_{1-6}$alkyl; and
R⁵ is:
hydrogen;
$C_{1-6}$alkyl;
hetero-$C_{1-6}$alkyl;
$C_{3-7}$cycloalkyl;
aryl;
heteroaryl;
heterocyclyl;
$C_{3-7}$cycloalkyl-$C_{1-6}$alkyl;
aryl-$C_{1-6}$alkyl;
heteroaryl-$C_{1-6}$alkyl; or
heterocyclyl-$C_{1-6}$alkyl.

In certain embodiments of formula I, Ia or Ib, Ar¹ and Ar² each are phenyl optionally substituted with one, two or three groups each independently selected from:
$C_{1-6}$alkyl;
halo;
$C_{1-6}$alkoxy;
halo-$C_{1-6}$alkoxy;
halo-$C_{1-6}$alkyl;
hetero-$C_{1-6}$alkyl;
cyano;
$C_{1-6}$alkyl-amino;
di-$C_{1-6}$alkyl-amino;
nitro; and
—(CRᵃRᵇ)ₘ—X—R³ wherein:
m is 0;
X is C(O) or S(O)ₙ;
R³ is —NR⁴R⁵, and
R⁴ and R⁵ each independently is:
hydrogen; or
$C_{1-6}$alkyl.

In certain embodiments of formula I, Ia or Ib, Ar¹ is phenyl optionally substituted with one, two or three groups each selected independently from halo, halo-$C_{1-6}$alkyl, $C_{1-6}$alkyl and $C_{1-6}$alkoxy.

In certain embodiments of formula I, Ia or Ib, Ar¹ is phenyl optionally substituted with one, two or three groups each selected independently from halo and $C_{1-6}$alkoxy.

In certain embodiments of formula I, Ia or Ib, Ar¹ is phenyl substituted one, two or three times with a group or groups independently selected from chloro, fluoro, methyl and methoxy.

In certain embodiments of formula I, Ia or Ib, Ar¹ is 5-chloro-2-methoxy-phenyl, 5-chloro-2,4-dimethoxy-phenyl, phenyl, 4-methoxy-phenyl, 4-methoxy-2-methyl-phenyl, 2,5-dimethoxy-phenyl, 4-methoxy-phenyl, 4-chlorophenyl, 3,4-dichloro-phenyl and 3-chlorophenyl.

In certain embodiments of formula I, Ia or Ib, Ar¹ is 4-trifluoromethyl-phenyl, 4-aminosulfonyl-phenyl, 4-N-methylamino-phenyl or 4-N,N-dimethylamino-phenyl.

In certain embodiments of formula I, Ia or Ib, Ar¹ is phenyl substituted once or twice with methoxy and optionally substituted once with chloro.

In certain embodiments of formula I, Ia or Ib, Ar¹ is phenyl substituted one, two or three times with a group or groups independently selected from chloro and methoxy.

In certain embodiments of formula I, Ia or Ib, Ar¹ is 5-chloro-2-methoxy-phenyl, 5-chloro-2,4-dimethoxy-phenyl, phenyl, 4-methyl-phenyl, 2-methoxy-5-methyl-phenyl, 2-methyl-5-methoxy-phenyl, 4-methoxy-2-methyl-phenyl, 2,5-dimethoxy-phenyl, 4-methoxy-phenyl, 4-chloro-phenyl, 3,4-dichloro-phenyl, 3-chloro-phenyl, 2-methoxy-phenyl, 4-tert-butyl-phenyl, 2,4-dimethoxy-phenyl, 3-trifluoromethyl-phenyl, 4-methanesulfonyl-phenyl, 4-aminosulfonyl-phenyl, 4-trifluoromethyl-phenyl, 5-fluoro-2-methoxy-phenyl, 2-methoxy-5-trifluoromethyl-phenyl, 2-methoxy-5-tert-butyl-phenyl, 4-chloro-2-methoxy-phenyl, 2,4,5-trimethoxy-phenyl, 2,6-dimethoxy-phenyl, or 2,3-dimethoxy-phenyl.

In certain embodiments of formula I, Ia or Ib, Ar¹ is optionally substituted heteroaryl. Preferred heteroaryl include pyridinyl, pyrimidinyl, thienyl, furanyl, thiazolyl, oxazolyl, isothiazolyl and isoxaloyl, each of which may be optionally substituted with one or two groups each selected independently from halo, $C_{1-6}$alkyl and $C_{1-6}$alkoxy.

In certain embodiments of formula I, Ia or Ib, Ar¹ is pyridinyl or isoxaloyl, each of which may be optionally substituted with one or two groups each selected independently from halo, methyl and methoxy.

In certain embodiments of formula I, Ia or Ib, Ar² is phenyl optionally substituted once at the 4-position with halo, $C_{1-6}$alkyl, cyano, halo-$C_{1-6}$alkyl, $C_{1-6}$alkoxy or —(CRᵃRᵇ)ₘ—X—R³ wherein:
m is 0;
X is —SO₂—;
R³ is $C_{1-6}$alkyl or —NR⁴R⁵, and
R⁴ and R⁵ each independently is:
hydrogen; or
$C_{1-6}$alkyl.

In certain embodiments of formula I, Ia or Ib, Ar² is phenyl substituted at the 4-position with cyano, —SO₂—NR⁵R⁶, or —SO₂—CH₃.

In certain embodiments of formula I, Ia or Ib, Ar² is phenyl substituted at the 4-position with —SO₂—NR⁵R⁶.

In certain embodiments of formula I, Ia or Ib, Ar² is phenyl substituted at the 4-position with —SO₂NH₂ or —SO₂—CH₃.

In certain embodiments of formula I, Ia or Ib, Ar² is phenyl substituted at the 4-position with —SO₂NH₂.

In certain embodiments of formula I, Ia or Ib, Ar² is phenyl substituted at the 4-position with —SO₂CH₃.

In certain embodiments of formula I, Ia or Ib, Ar² is phenyl, 4-aminosulfonyl-phenyl, 4-methylaminosulfonyl-phenyl, 4-dimethylaminosulfonyl-phenyl, 4-trifluoromethyl-phenyl, 4-methyl-phenyl, 4-chloro-phenyl, 4-methanesulfonyl-phenyl, 4-methoxy-phenyl, 4-cyano-phenyl or 4-bromo-phenyl.

In certain embodiments of formula I, Ia or Ib, $R^1$ and $R^2$ are $C_{1-6}$alkyl.

In certain embodiments of formula I, Ia or Ib, one of $R^1$ and $R^2$ is hydrogen and the other is $C_{1-6}$alkyl.

In certain embodiments of formula I, Ia or Ib, one of $R^1$ and $R^2$ is hydrogen and the other is methyl or ethyl.

In certain embodiments of formula I, Ia or Ib, $R^1$ and $R^2$ are methyl.

In certain embodiments of formula I, Ia or Ib, $R^1$ and $R^2$ are hydrogen.

In certain embodiments of the invention, the subject compounds are of formula II:

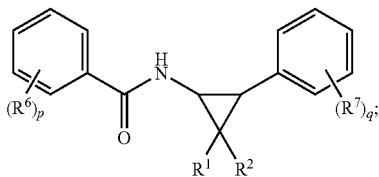

II wherein:
  p and q each independently is from 0 to 3;
  $R^1$ and $R^2$ are $C_{1-6}$alkyl; and
  $R^6$ and $R^7$ each independently is:
    $C_{1-6}$alkyl;
    halo;
    $C_{1-6}$alkoxy;
    halo-$C_{1-6}$alkoxy;
    halo-$C_{1-6}$alkyl;
    hetero-$C_{1-6}$alkyl;
    cyano;
    $C_{1-6}$alkyl-amino;
    di-$C_{1-6}$alkyl-amino;
    nitro; and
    —$(CR^aR^b)_m$—X—$R^3$ wherein:
      m is 0;
      X is —$SO_2$—;
      $R^3$ is $C_{1-6}$alkyl or —$NR^4R^5$, and
        $R^4$ and $R^5$ each independently is:
          hydrogen; or
          $C_{1-6}$alkyl.

In certain embodiments the compounds of the invention may be of formula IIa or IIb:

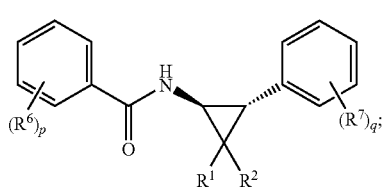

IIa

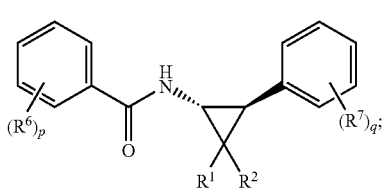

IIb wherein p, q, $R^1$, $R^2$, $R^6$ and $R^7$ are as defined herein.

In certain embodiments of formula II, IIa or IIb, $R^1$ and $R^2$ are methyl.

In certain embodiments of formula II, IIa or IIb, one of $R^1$ and $R^2$ is hydrogen and the other is methyl or ethyl.

In certain embodiments of formula II, IIa or IIb, $R^1$ and $R^2$ are hydrogen.

In certain embodiments of formula II, IIa or IIb, p is from 0 to 3 and each $R^6$ is independently:
  $C_{1-6}$alkyl;
  halo;
  $C_{1-6}$alkoxy;
  halo-$C_{1-6}$alkoxy;
  halo-$C_{1-6}$alkyl;
  hetero-$C_{1-6}$alkyl;
  cyano;
  $C_{1-6}$alkyl-amino;
  di-$C_{1-6}$alkyl-amino;
  nitro; and
  —$(CR^aR^b)_m$—X—$R^3$ wherein:
    m is 0;
    X is —$SO_2$—;
    $R^3$ is $C_{1-6}$alkyl or —$NR^4R^5$, and
      $R^4$ and $R^5$ each independently is:
        hydrogen; or
        $C_{1-6}$alkyl.

In certain embodiments of formula II, IIa or IIb, q is 1 and $R^7$ is:
  $C_{1-6}$alkyl;
  halo;
  $C_{1-6}$alkoxy;
  halo-$C_{1-6}$alkoxy;
  halo-$C_{1-6}$alkyl;
  hetero-$C_{1-6}$alkyl;
  cyano;
  $C_{1-6}$alkyl-amino;
  di-$C_{1-6}$alkyl-amino;
  nitro; and
  —$(CR^aR^b)_m$—X—$R^3$ wherein:
    m is 0;
    X is —$SO_2$—;
    $R^3$ is $C_{1-6}$alkyl or —$NR^4R^5$, and
      $R^4$ and $R^5$ each independently is:
        hydrogen; or
        $C_{1-6}$alkyl.

In certain embodiments of formula II, IIa or IIb, p is from 1 to 3 and each $R^6$ is independently:
  $C_{1-6}$alkyl;
  halo;
  $C_{1-6}$alkoxy;
  halo-$C_{1-6}$alkoxy; or
  halo-$C_{1-6}$alkyl.

In certain embodiments of formula II, IIa or IIb, p is from 1 to 3 and each $R^6$ is independently methyl, fluoro, chloro, methoxy or trifluoromethyl.

In certain embodiments of formula II, IIa or IIb, p is from 1 to 3 and each $R^6$ is independently chloro or methoxy.

In certain embodiments of formula II, IIa or IIb, q is 1 and $R^7$ is halo, cyano;, $C_{1-6}$alkyl, halo-$C_{1-6}$alkyl $C_{1-6}$alkoxy; or —$(CR^aR^b)_m$—X—$R^3$ wherein:
  m is 0;
  X is —$SO_2$—;
  $R^3$ is $C_{1-6}$alkyl or —$NR^4R^5$, and
    $R^4$ and $R^5$ each independently is:
      hydrogen; or
      $C_{1-6}$alkyl.

In certain embodiments of formula II, IIa or IIb, q is one and $R^7$ is at the 4-position of the phenyl ring.

In certain embodiments of formula II, IIa or IIb, q is 1 and $R^7$ is $-SO_2NR^4R^5$.

In certain embodiments of formula II, IIa or IIb, q is 1 and $R^7$ is $-SO_2NH_2$.

In certain embodiments of the invention, the subject compounds are of formula III:

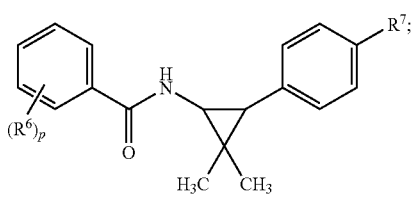

wherein:
p is from 0 to 3;
each $R^6$ is independently selected from:
  $C_{1-6}$alkyl;
  halo;
  $C_{1-6}$alkoxy;
  halo-$C_{1-6}$alkoxy; or
  halo-$C_{1-6}$alkyl; and
$R^7$ is:
  halo;
  cyano;
  $C_{1-6}$alkyl;
  $C_{1-6}$alkoxy; or
  $-(CR^aR^b)_m-X-R^3$ wherein:
    m is 0;
    X is $-SO_2-$;
    $R^3$ is $C_{1-6}$alkyl or $-NR^4R^5$, and
    $R^4$ and $R^5$ each independently is:
      hydrogen; or
      $C_{1-6}$alkyl.

In certain embodiments the subject compounds may be of formula IIIa or IIIb:

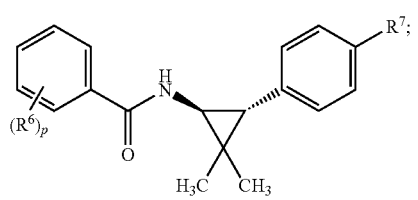

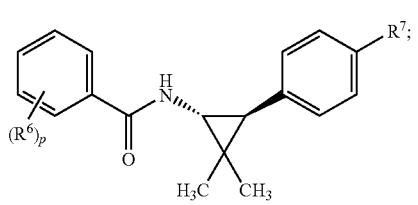

wherein p, $R^6$ and $R^7$ are as defined herein.

In certain embodiments of formula III, IIIa or IIIb, p is from 0 to 3 and each $R^6$ is independently:
  $C_{1-6}$alkyl;
  halo;
  $C_{1-6}$alkoxy;
  halo-$C_{1-6}$alkoxy;
  halo-$C_{1-6}$alkyl;
  hetero-$C_{1-6}$alkyl;
  cyano;
  $C_{1-6}$alkyl-amino;
  di-$C_{1-6}$alkyl-amino;
  nitro; and
  $-(CR^aR^b)_m-X-R^3$ wherein:
    m is 0;
    X is $-SO_2-$;
    $R^3$ is $C_{1-6}$alkyl or $-NR^4R^5$, and
    $R^4$ and $R^5$ each independently is:
      hydrogen; or
      $C_{1-6}$alkyl.

In certain embodiments of formula III, IIIa or IIIb, p is from 1 to 3 and each $R^6$ is independently:
  $C_{1-6}$alkyl;
  halo;
  $C_{1-6}$alkoxy;
  halo-$C_{1-6}$alkoxy; or
  halo-$C_{1-6}$alkyl.

In certain embodiments of formula III, IIIa or IIIb, p is from 1 to 3 and each $R^6$ is independently methyl, fluoro, chloro, methoxy or trifluoromethyl.

In certain embodiments of formula III, IIIa or IIIb, p is 2 or 3 and each $R^6$ is independently chloro or methoxy.

In certain embodiments of formula III, IIIa or IIIb, $R^7$ is $-(CR^aR^b)_m-X-R^3$ wherein:
  m is 0;
  X is $-SO_2-$;
  $R^3$ is $C_{1-6}$alkyl or $-NR^4R^5$, and
  $R^4$ and $R^5$ each independently is:
    hydrogen; or
    $C_{1-6}$alkyl.

In certain embodiments of formula III, IIIa or IIIb, $R^7$ is $-SO_2NR^5R^6$.

In certain embodiments of formula III, IIIa or IIIb, $R^7$ is $-SO_2NH_2$.

Where any of $R^1$, $R^2$, $R^3$, $R^4$, $R^5$, $R^6$, $R^7$, $R^a$ or $R^b$ herein are alkyl or contain an alkyl moiety, such alkyl is preferably lower alkyl, i.e. $C_1$-$C_6$alkyl, and more preferably $C_1$-$C_4$alkyl.

Representative compounds in accordance with the methods of the invention are shown in Table 1. Compounds identified as "cis" or "trans" were isolated as racemates.

TABLE 1

| # | Structure | Name | MP/M + H |
|---|---|---|---|
| 1 | 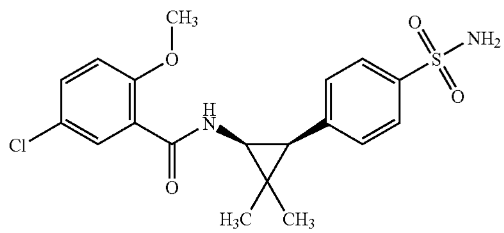 | 5-Chloro-N-[cis-2,2-dimethyl-3-(4-sulfamoyl-phenyl)-cyclopropyl]-2-methoxy-benzamide | 220-222° C. |
| 2 | 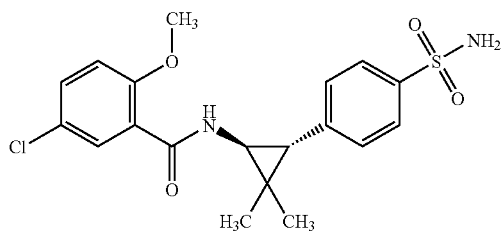 | 5-Chloro-N-[trans-2,2-dimethyl-3-(4-sulfamoyl-phenyl)-cyclopropyl]-2-methoxy-benzamide | 203-204° C. |
| 3 | 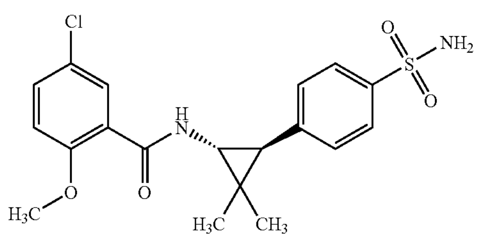 | 5-Chloro-N-[(1R,3S)-2,2-dimethyl-3-(4-sulfamoyl-phenyl)-cyclopropyl]-2-methoxy-benzamide | 99.9-103.3° C. |
| 4 | 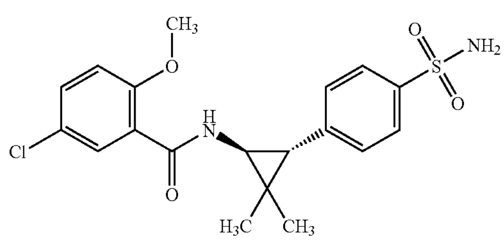 | 5-Chloro-N-[(1S,3R)-2,2-dimethyl-3-(4-sulfamoyl-phenyl)-cyclopropyl]-2-methoxy-benzamide | 96.8-101.1° C. |
| 5 | 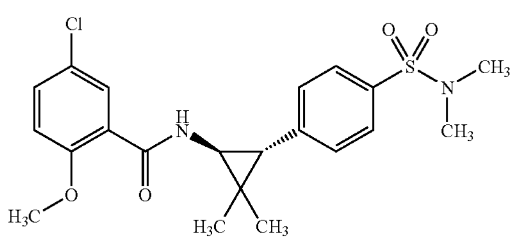 | 5-Chloro-N-[3-(4-dimethylsulfamoyl-phenyl)-trans-2,2-dimethyl-cyclopropyl]-2-methoxy-benzamide | 437 |
| 6 | 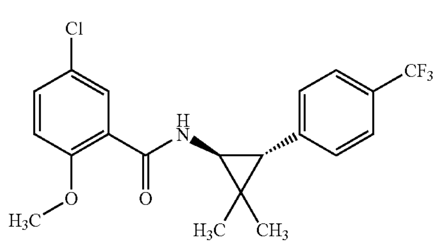 | 5-Chloro-N-[trans-2,2-dimethyl-3-(4-trifluoromethyl-phenyl)-cyclopropyl]-2-methoxy-benzamide | 398 |

TABLE 1-continued

| # | Structure | Name | MP/M + H |
|---|---|---|---|
| 7 | 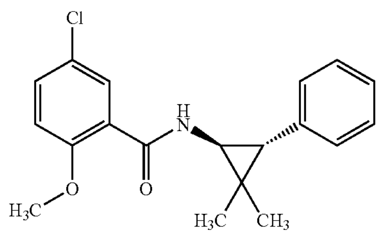 | 5-Chloro-N-[trans-2,2-dimethyl-3-phenyl-cyclopropyl]-2-methoxy-benzamide | 330 |
| 8 | 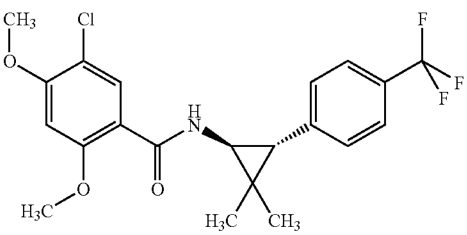 | 5-Chloro-N-[trans-2,2-dimethyl-3-(4-trifluoromethyl-phenyl)-cyclopropyl]-2,4-dimethoxy-benzamide | 428 |
| 9 | 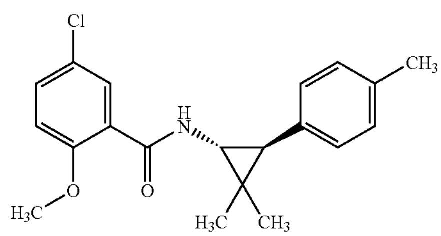 | 5-Chloro-N-[trans-2,2-dimethyl-3-p-tolyl-cyclopropyl]-2-methoxy-benzamide | 344 |
| 10 | 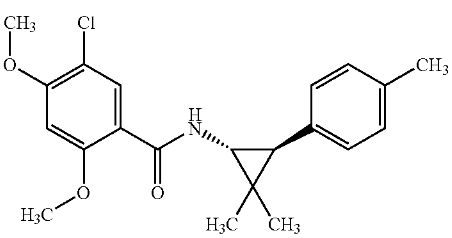 | 5-Chloro-N-[trans-2,2-dimethyl-3-p-tolyl-cyclopropyl]-2,4-dimethoxy-benzamide | 148.3-150.9° C. |
| 11 | 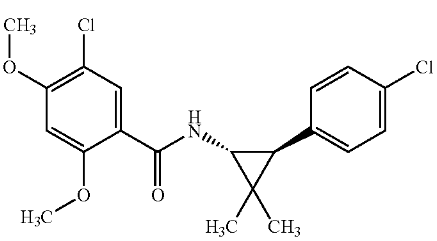 | 5-Chloro-N-[3-(4-chloro-phenyl)-trans-2,2-dimethyl-cyclopropyl]-2,4-dimethoxy-benzamide | 166.4-167.3° C. |
| 12 | 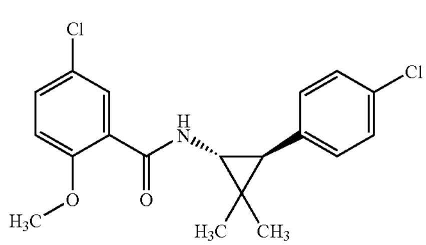 | 5-Chloro-N-[3-(4-chloro-phenyl)-trans-2,2-dimethyl-cyclopropyl]-2-methoxy-benzamide | 365 |

TABLE 1-continued

| # | Structure | Name | MP/M + H |
|---|---|---|---|
| 13 | 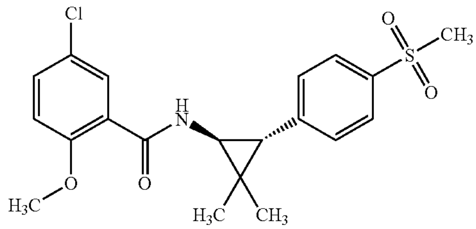 | 5-Chloro-N-[3-(4-methanesulfonyl-phenyl)-trans-2,2-dimethyl-cyclopropyl]-2-methoxy-benzamide | 408 |
| 14 | 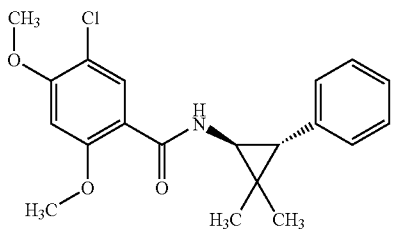 | 5-Chloro-N-[trans-2,2-dimethyl-3-phenyl-cyclopropyl]-2,4-dimethoxy-benzamide | 360 |
| 15 | 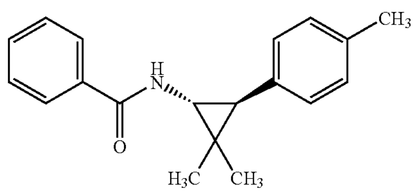 | N-[(Trans-2,2-Dimethyl-3-p-tolyl-cyclopropyl]-benzamide | 280 |
| 16 | 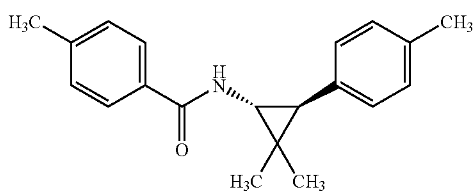 | N-[trans-2,2-Dimethyl-3-p-tolyl-cyclopropyl]-4-methyl-benzamide | 294 |
| 17 | 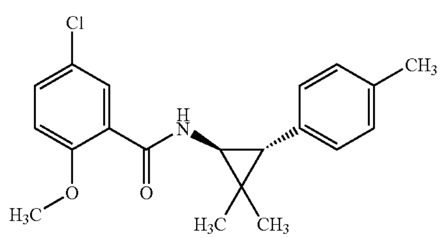 | N-[trans-2,2-Dimethyl-3-p-tolyl-cyclopropyl]-2-methoxy-5-methyl-benzamide | 324 |
| 18 | 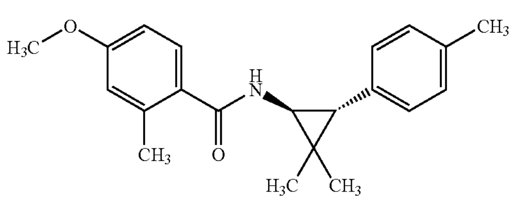 | N-[trans-2,2-Dimethyl-3-p-tolyl-cyclopropyl]-4-methoxy-2-methyl-benzamide | 324 |
| 19 | 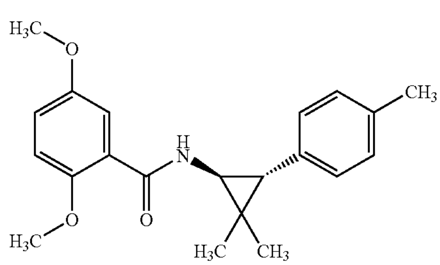 | N-[trans-2,2-Dimethyl-3-p-tolyl-cyclopropyl]-2,5-dimethoxy-benzamide | 340 |

TABLE 1-continued

| # | Structure | Name | MP/M + H |
|---|---|---|---|
| 20 | 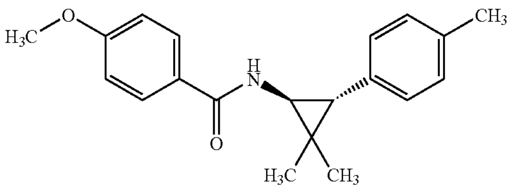 | N-[trans-2,2-Dimethyl-3-p-tolyl-cyclopropyl]-4-methoxy-benzamide | 310 |
| 21 | 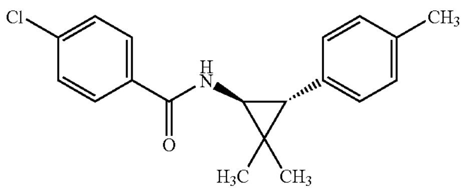 | 4-Chloro-N-[trans-2,2-dimethyl-3-p-tolyl-cyclopropyl]-benzamide | 314 |
| 22 | 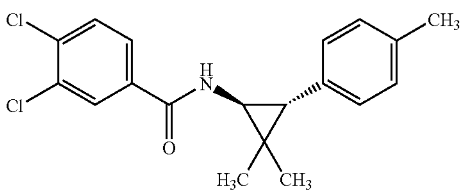 | 3,4-Dichloro-N-[(trans-2,2-dimethyl-3-p-tolyl-cyclopropyl]-benzamide | 349 |
| 23 | 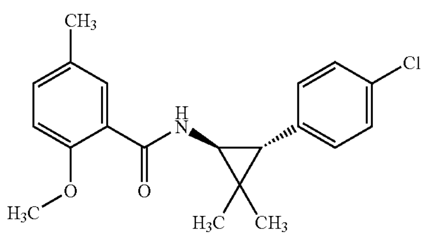 | N-[3-(4-Chloro-phenyl)-trans-2,2-dimethyl-cyclopropyl]-2-methoxy-5-methyl-benzamide | 344 |
| 24 | 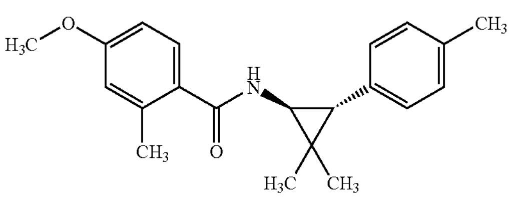 | N-[3-(4-Chloro-phenyl)-trans-2,2-dimethyl-cyclopropyl]-4-methoxy-2-methyl-benzamide | 344 |
| 25 | 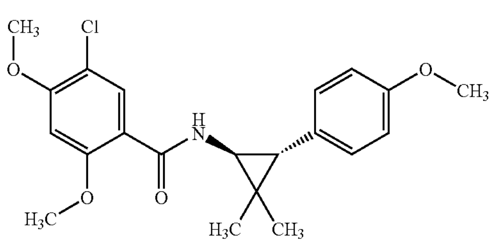 | 5-Chloro-2,4-dimethoxy-N-[3-(4-methoxy-phenyl)-trans-2,2-dimethyl-cyclopropyl]-benzamide | 390 |
| 26 | 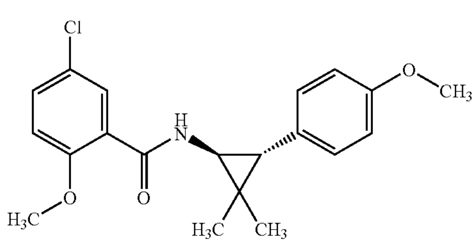 | 5-Chloro-2-methoxy-N-[3-(4-methoxy-phenyl)-trans-2,2-dimethyl-cyclopropyl]-benzamide | 360 |

TABLE 1-continued

| # | Structure | Name | MP/M + H |
|---|---|---|---|
| 27 | 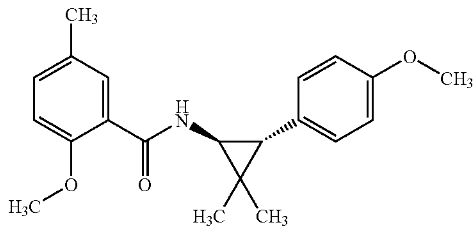 | 2-Methoxy-N-[3-(4-methoxy-phenyl)-trans-2,2-dimethyl-cyclopropyl]-5-methyl-benzamide | 340 |
| 28 | 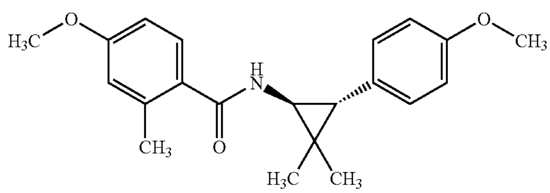 | 4-Methoxy-N-[3-(4-methoxy-phenyl)-trans-2,2-dimethyl-cyclopropyl]-2-methyl-benzamide | 340 |
| 29 | 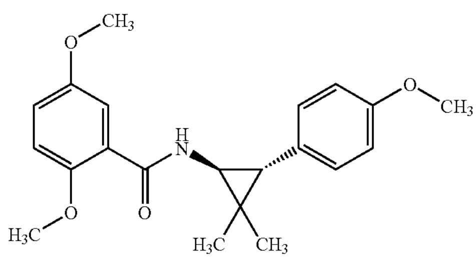 | 2,5-Dimethoxy-N-[3-(4-methoxy-phenyl)-trans-2,2-dimethyl-cyclopropyl]-benzamide | 356 |
| 30 | 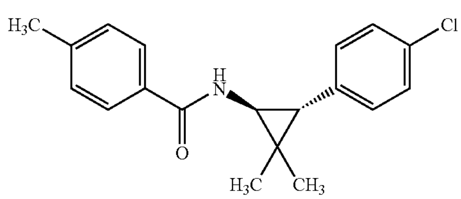 | N-[3-(4-Chloro-phenyl)-trans-2,2-dimethyl-cyclopropyl]-4-methyl-benzamide | 314 |
| 31 | 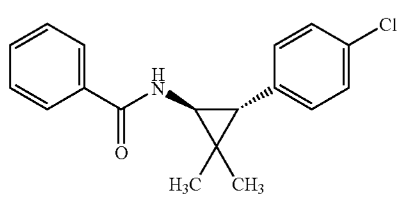 | N-[3-(4-Chloro-phenyl)-trans-2,2-dimethyl-cyclopropyl]-benzamide | 300 |
| 32 | 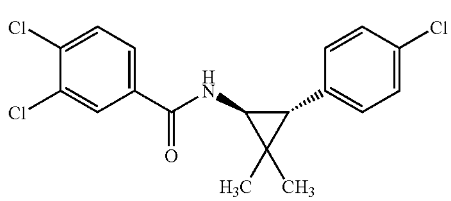 | 3,4-Dichloro-N-[3-(4-chloro-phenyl)-trans-2,2-dimethyl-cyclopropyl]-benzamide | 369 |
| 33 | 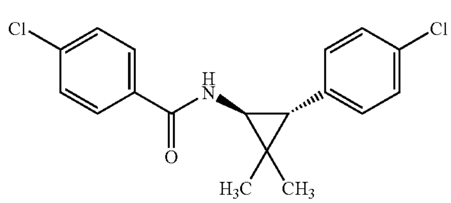 | 4-Chloro-N-[3-(4-chloro-phenyl)-trans-2,2-dimethyl-cyclopropyl]-benzamide | 335 |

TABLE 1-continued

| # | Structure | Name | MP/M + H |
|---|---|---|---|
| 34 | 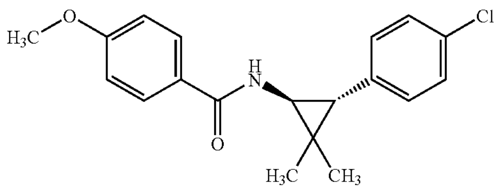 | N-[3-(4-Chloro-phenyl)-trans-2,2-dimethyl-cyclopropyl]-4-methoxy-benzamide | 330 |
| 35 | 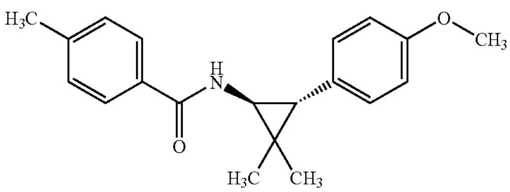 | N-[3-(4-Methoxy-phenyl)-trans-2,2-dimethyl-cyclopropyl]-4-methyl-benzamide | 310 |
| 36 | 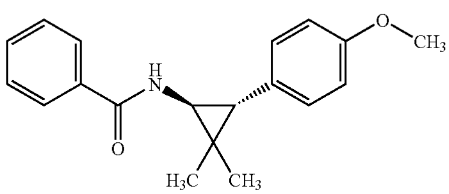 | N-[3-(4-Methoxy-phenyl)-trans-2,2-dimethyl-cyclopropyl]-benzamide | 296 |
| 37 | 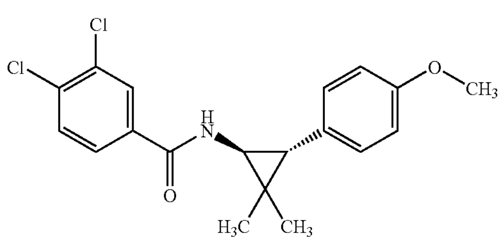 | 3,4-Dichloro-N-[3-(4-methoxy-phenyl)-trans-2,2-dimethyl-cyclopropyl]-benzamide | 365 |
| 38 | 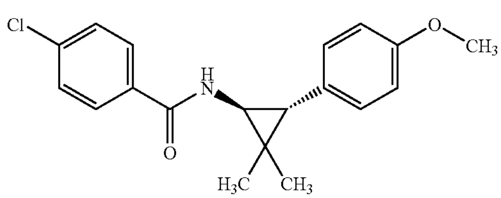 | 4-Chloro-N-[3-(4-methoxy-phenyl)-trans-2,2-dimethyl-cyclopropyl]-benzamide | 330 |
| 39 | 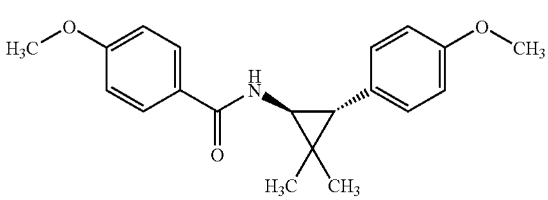 | 4-Methoxy-N-[3-(4-methoxy-phenyl)-trans-2,2-dimethyl-cyclopropyl]-benzamide | 326 |
| 40 | 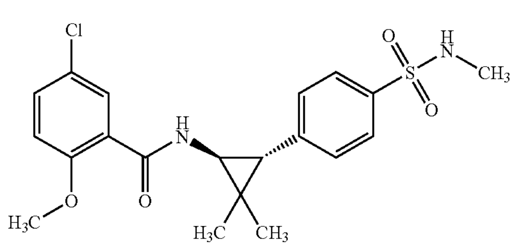 | 5-Chloro-N-[(1S,3R)-2,2-dimethyl-3-(4-methylsulfamoyl-phenyl)-cyclopropyl]-2-methoxy-benzamide | 423 |

TABLE 1-continued

| # | Structure | Name | MP/M + H |
|---|---|---|---|
| 41 | 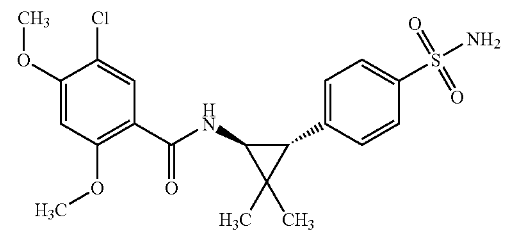 | 5-Chloro-N-[(1S,3R)-2,2-dimethyl-3-(4-sulfamoyl-phenyl)-cyclopropyl]-2,4-dimethoxy-benzamide | 439 |
| 42 | 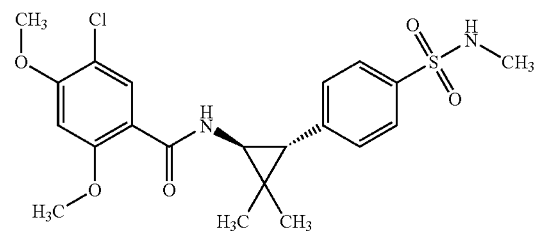 | 5-Chloro-N-[(1S,3R)-2,2-dimethyl-3-(4-methylsulfamoyl-phenyl)-cyclopropyl]-2,4-dimethoxy-benzamide | 453 |
| 43 | 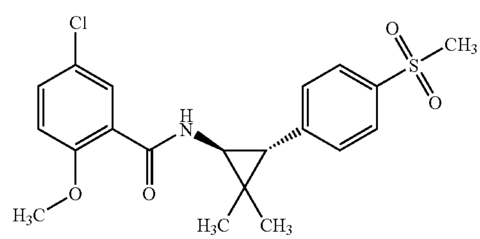 | 5-Chloro-N-[3-(4-methanesulfonyl-phenyl)-(1S,3R)-2,2-dimethyl-cyclopropyl]-2-methoxy-benzamide | 408 |
| 44 | 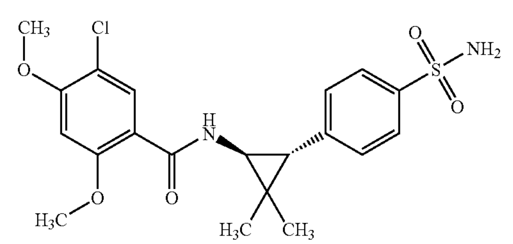 | 5-Chloro-N-[trans-2,2-dimethyl-3-(4-sulfamoyl-phenyl)-cyclopropyl]-2,4-dimethoxy-benzamide | 439 |
| 45 | 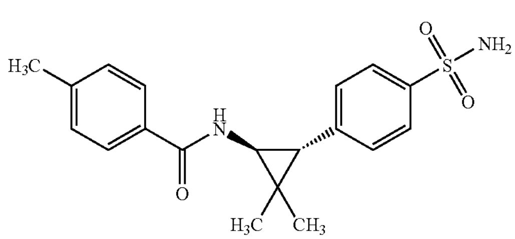 | N-[Trans-2,2-Dimethyl-3-(4-sulfamoyl-phenyl)-cyclopropyl]-4-methyl-benzamide | 359 |
| 46 | 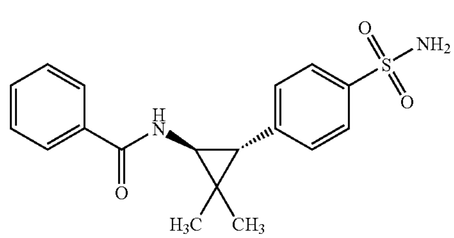 | N-[Trans-2,2-Dimethyl-3-(4-sulfamoyl-phenyl)-cyclopropyl]-benzamide | 345 |

TABLE 1-continued

| # | Structure | Name | MP/M + H |
|---|---|---|---|
| 47 | 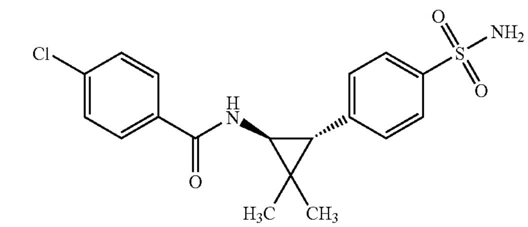 | 4-Chloro-N-[trans-2,2-dimethyl-3-(4-sulfamoyl-phenyl)-cyclopropyl]-benzamide | 379 |
| 48 | 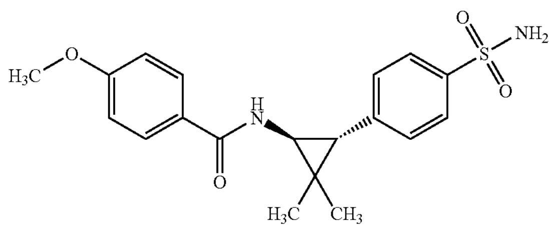 | N-[Trans-2,2-Dimethyl-3-(4-sulfamoyl-phenyl)-cyclopropyl]-4-methoxy-benzamide | 375 |
| 49 | 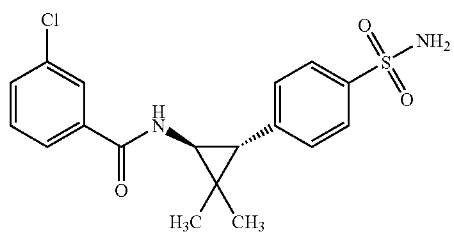 | 3-Chloro-N-[trans-2,2-dimethyl-3-(4-sulfamoyl-phenyl)-cyclopropyl]-benzamide | 379 |
| 50 | 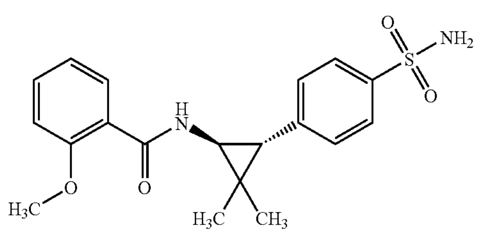 | N-[trans-2,2-Dimethyl-3-(4-sulfamoyl-phenyl)-cyclopropyl]-2-methoxy-benzamide | 375 |
| 51 | 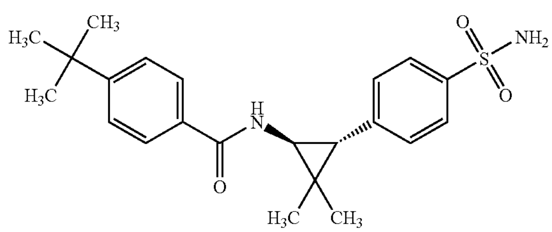 | 4-tert-Butyl-N-[trans-2,2-dimethyl-3-(4-sulfamoyl-phenyl)-cyclopropyl]-benzamide | 401 |
| 52 | 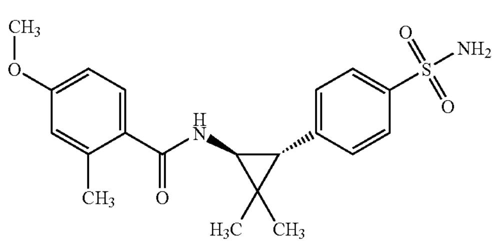 | N-[Trans-2,2-Dimethyl-3-(4-sulfamoyl-phenyl)-cyclopropyl]-4-methoxy-2-methyl-benzamide | 389 |

TABLE 1-continued

| # | Structure | Name | MP/M + H |
|---|---|---|---|
| 53 | 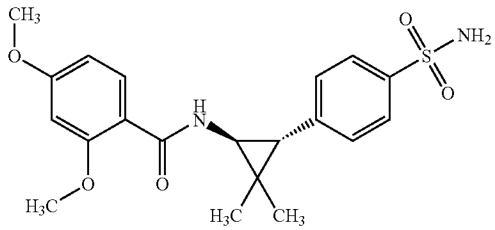 | N-[Trans-2,2-Dimethyl-3-(4-sulfamoyl-phenyl)-cyclopropyl]-2,4-dimethoxy-benzamide | 405 |
| 54 | 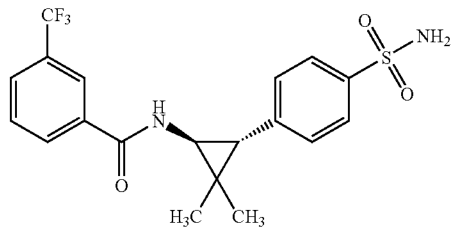 | N-[Trans-2,2-Dimethyl-3-(4-sulfamoyl-phenyl)-cyclopropyl]-3-trifluoromethyl-benzamide | 413 |
| 55 | 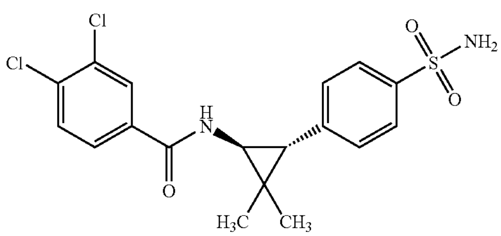 | 3,4-Dichloro-N-[trans-2,2-dimethyl-3-(4-sulfamoyl-phenyl)-cyclopropyl]-benzamide | 414 |
| 56 | 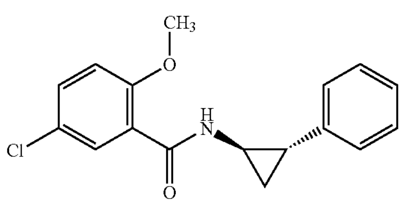 | 5-Chloro-2-methoxy-N-(trans-2-phenyl-cyclopropyl)-benzamide | 302 |
| 57 | 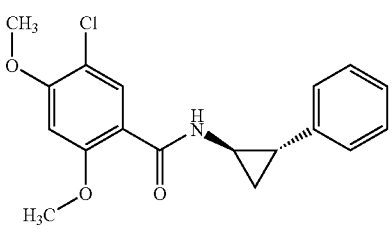 | 5-Chloro-2,4-dimethoxy-N-(trans-2-phenyl-cyclopropyl)-benzamide | 302 |
| 58 | 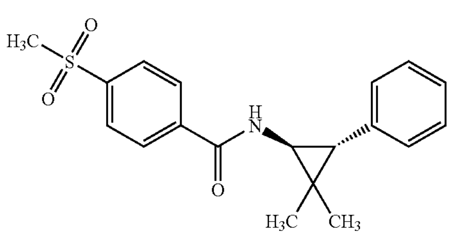 | N-(Trans-2,2-Dimethyl-3-phenyl-cyclopropyl)-4-methanesulfonyl-benzamide | 344 |

TABLE 1-continued

| # | Structure | Name | MP/M + H |
|---|---|---|---|
| 59 | 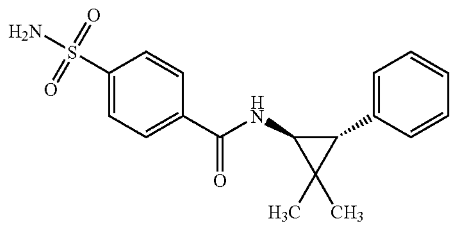 | N-(Trans-2,2-Dimethyl-3-phenyl-cyclopropyl)-4-sulfamoyl-benzamide | 345 |
| 60 | 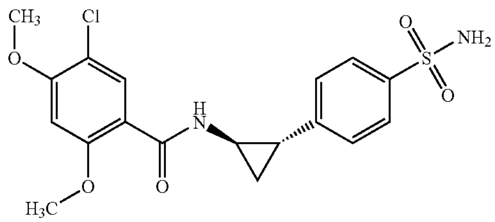 | 5-Chloro-2,4-dimethoxy-N-[trans-2-(4-sulfamoyl-phenyl)-cyclopropyl]-benzamide | 411 |
| 61 | 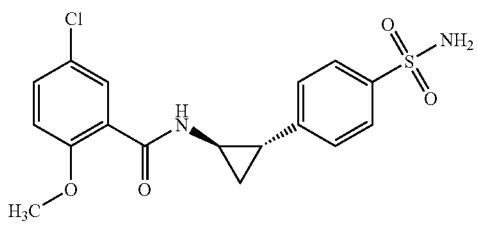 | 5-Chloro-2-methoxy-N-[trans-2-(4-sulfamoyl-phenyl)-cyclopropyl]-benzamide | 381 |
| 62 | 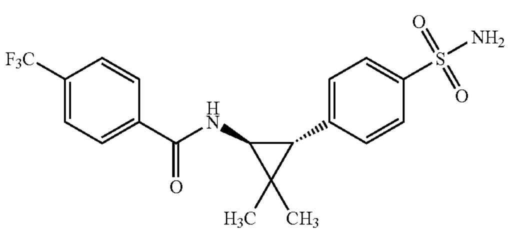 | N-[Trans-2,2-Dimethyl-3-(4-sulfamoyl-phenyl)-cyclopropyl]-4-trifluoromethyl-benzamide | 413 |
| 63 | 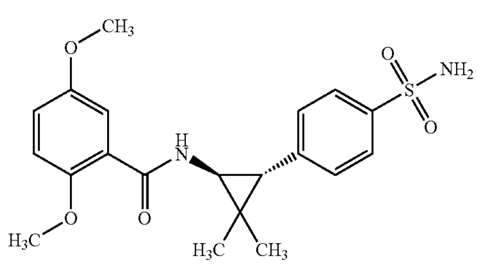 | N-[Trans-2,2-Dimethyl-3-(4-sulfamoyl-phenyl)-cyclopropyl]-2,5-dimethoxy-benzamide | 405 |
| 64 | 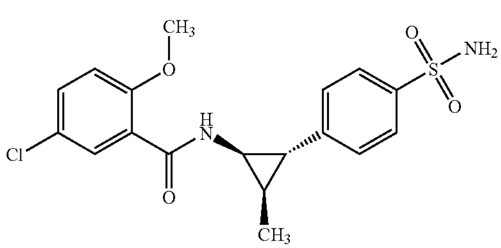 | 5-Chloro-2-methoxy-N-[trans-2-methyl-3-(4-sulfamoyl-phenyl)-cyclopropyl]-benzamide | 395 |

| # | Structure | Name | MP/M + H |
|---|---|---|---|
| 65 | 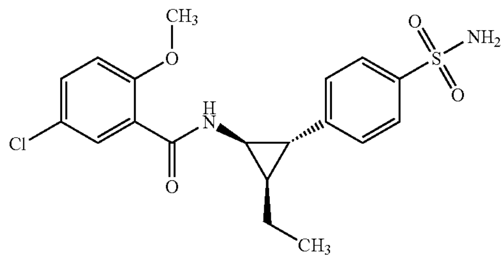 | 5-Chloro-N-[trans-2-ethyl-3-(4-sulfamoyl-phenyl)-cyclopropyl]-2-methoxy-benzamide | 409 |
| 66 | 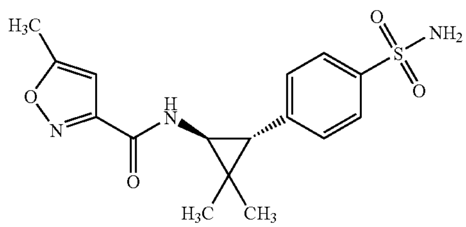 | 5-Methyl-isoxazole-3-carboxylic acid [trans-2,2-dimethyl-3-(4-sulfamoyl-phenyl)-cyclopropyl]-amide | 350 |
| 67 | 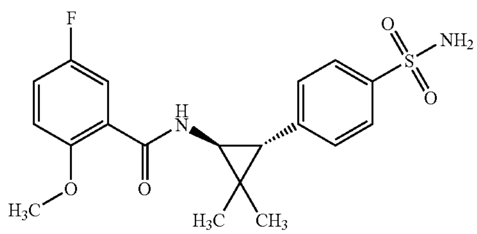 | N-[Trans-2,2-Dimethyl-3-(4-sulfamoyl-phenyl)-cyclopropyl]-5-fluoro-2-methoxy-benzamide | 172.6-173.6° C. |
| 68 | 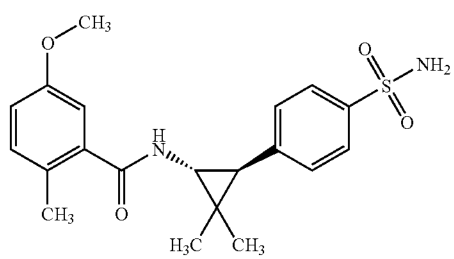 | N-[Trans-2,2-Dimethyl-3-(4-sulfamoyl-phenyl)-cyclopropyl]-5-methoxy-2-methyl-benzamide | 99-100° C. |
| 69 | 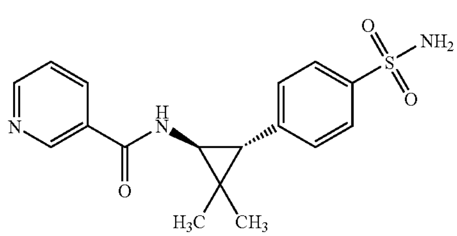 | N-[Trans-2,2-Dimethyl-3-(4-sulfamoyl-phenyl)-cyclopropyl]-nicotinamide | 346 |
| 70 | 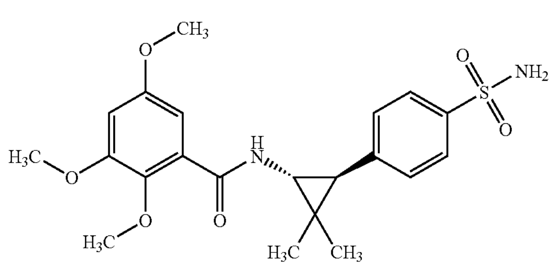 | N-[Trans-2,2-Dimethyl-3-(4-sulfamoyl-phenyl)-cyclopropyl]-2,3,5-trimethoxy-benzamide | 144-145° C. |

TABLE 1-continued

| # | Structure | Name | MP/M + H |
|---|---|---|---|
| 71 | 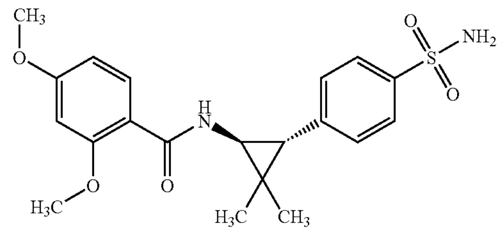 | N-[(1S,3R)-2,2-Dimethyl-3-(4-sulfamoyl-phenyl)-cyclopropyl]-2,4-dimethoxy-benzamide | 405 |
| 72 | 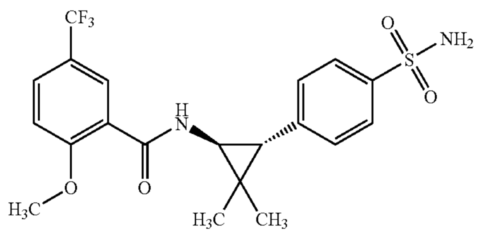 | N-[Trans-2,2-Dimethyl-3-(4-sulfamoyl-phenyl)-cyclopropyl]-2-methoxy-5-trifluoromethyl-benzamide | 443 |
| 73 | 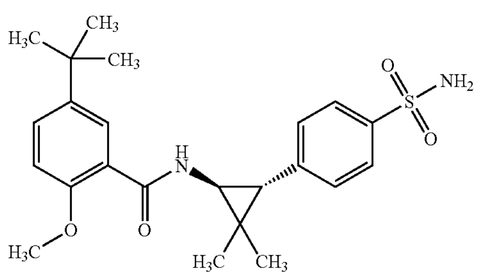 | 5-tert-Butyl-N-[trans-2,2-dimethyl-3-(4-sulfamoyl-phenyl)-cyclopropyl]-2-methoxy-benzamide | 431 |
| 74 | 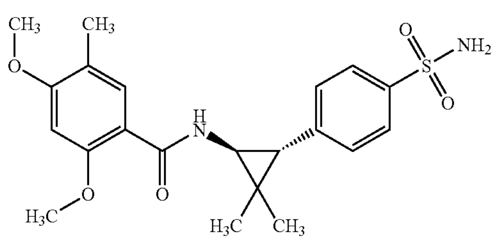 | N-[Trans-2,2-Dimethyl-3-(4-sulfamoyl-phenyl)-cyclopropyl]-2,4-dimethoxy-5-methyl-benzamide | 419 |
| 75 | 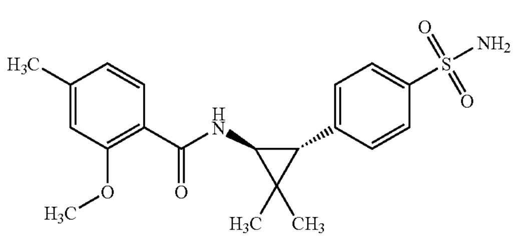 | N-[Trans-2,2-Dimethyl-3-(4-sulfamoyl-phenyl)-cyclopropyl]-2-methoxy-4-methyl-benzamide | 389 |
| 76 | 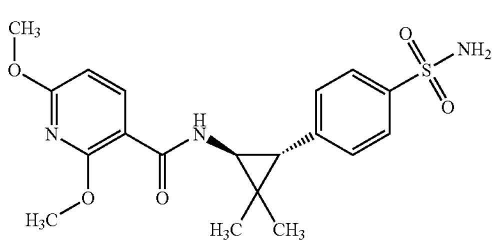 | N-[Trans-2,2-Dimethyl-3-(4-sulfamoyl-phenyl)-cyclopropyl]-2,6-dimethoxy-nicotinamide | 406 |

TABLE 1-continued

| # | Structure | Name | MP/M + H |
|---|---|---|---|
| 77 | 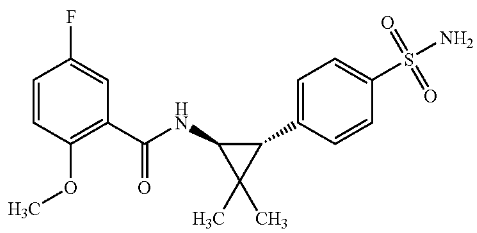 | N-[(1S,3R)-2,2-Dimethyl-3-(4-sulfamoyl-phenyl)-cyclopropyl]-5-fluoro-2-methoxy-benzamide | 164-165° C. |
| 78 | 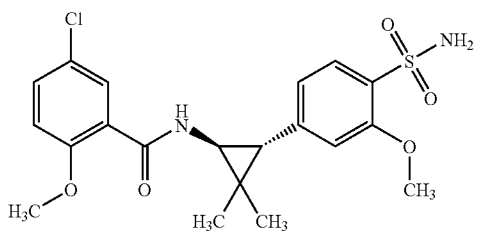 | 5-Chloro-2-methoxy-N-[trans-3-(3-methoxy-4-sulfamoyl-phenyl)-2,2-dimethyl-cyclopropyl]-benzamide | 193-194° C. |
| 79 | 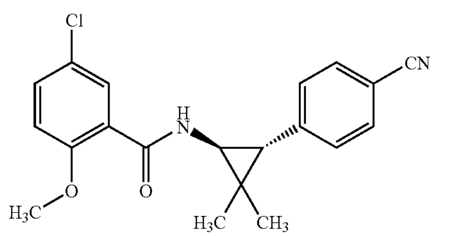 | 5-Chloro-N-[trans-3-(4-cyano-phenyl)-2,2-dimethyl-cyclopropyl]-2-methoxy-benzamide | 157.2-157.6° C. |
| 80 | 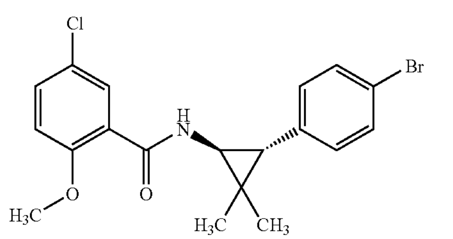 | N-[Trans-3-(4-Bromo-phenyl)-2,2-dimethyl-cyclopropyl]-5-chloro-2-methoxy-benzamide | 125.5-126.9° C. |
| 81 | 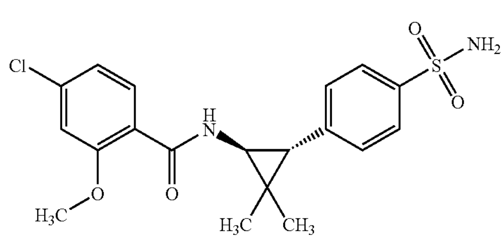 | 4-Chloro-N-[trans-2,2-dimethyl-3-(4-sulfamoyl-phenyl)-cyclopropyl]-2-methoxy-benzamide | 409 |
| 82 | 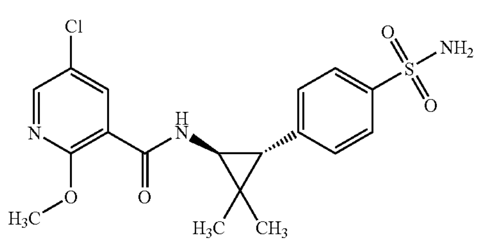 | 5-Chloro-N-[2(trans-2-dimethyl-3-(4-sulfamoyl-phenyl)-cyclopropyl]-2-methoxy-nicotinamide | 410 |

TABLE 1-continued

| # | Structure | Name | MP/M + H |
|---|---|---|---|
| 83 | 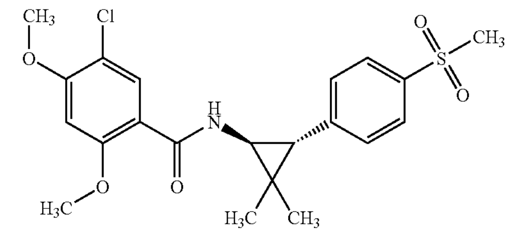 | 5-Chloro-N-[trans-3-(4-methanesulfonyl-phenyl)-2,2-dimethyl-cylopropyl]-2,4-dimethoxy-benzamide | 438 |
| 84 | 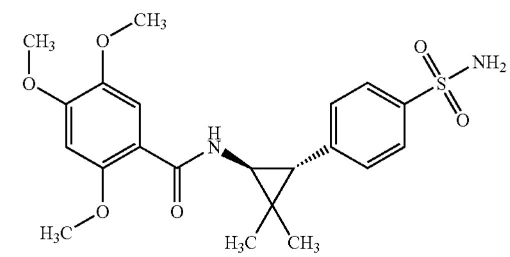 | N-[Trans-2,2-Dimethyl-3-(4-sulfamoyl-phenyl)-cyclopropyl]-2,4,5-trimethoxy-benzamide | 435 |
| 85 | 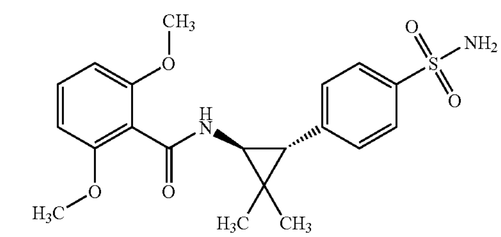 | N-[Trans-2,2-Dimethyl-3-(4-sulfamoyl-phenyl)-cyclopropyl]-2,6-dimethoxy-benzamide | 405 |
| 86 | 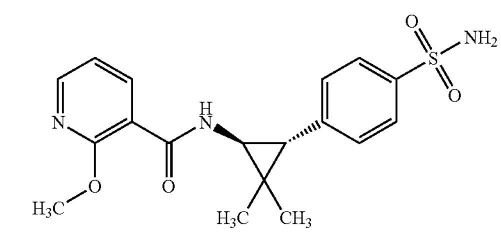 | N-[Trans-2,2-Dimethyl-3-(4-sulfamoyl-phenyl)-cyclopropyl]-2-methoxy-nicotinamide | 376 |
| 87 | 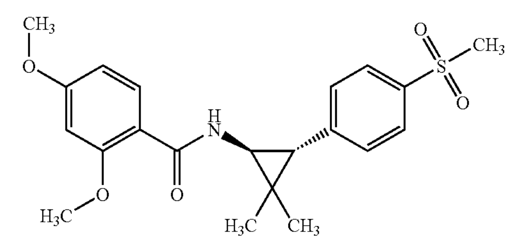 | N-[Trans-3-(4-Methanesulfonyl-phenyl)-2,2-dimethyl-cyclopropyl]-2,4-dimethoxy-benzamide | 404 |
| 88 | 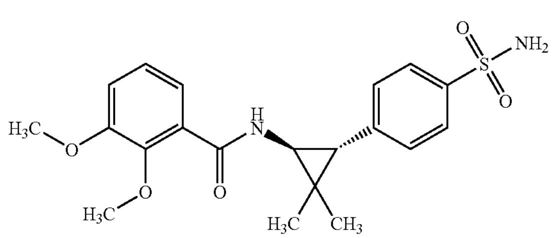 | N-[Trans-2,2-Dimethyl-3-(4-sulfamoyl-phenyl)-cyclopropyl]-2,3-dimethoxy-benzamide | 405 |

TABLE 1-continued

| # | Structure | Name | MP/M + H |
|---|---|---|---|
| 89 | 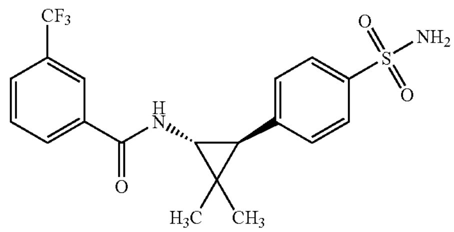 | N-[Trans-2,2-Dimethyl-3-(4-sulfamoyl-phenyl)-cyclopropyl]-3-trifluoromethyl-benzamide | 413 |
| 90 | 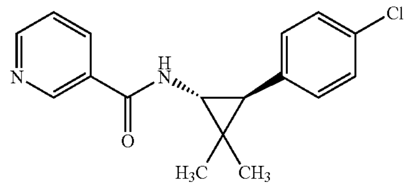 | N-[Trans-3-(4-Chloro-phenyl)-2,2-dimethyl-cyclopropyl]-nicotinamide | 301 |
| 91 | 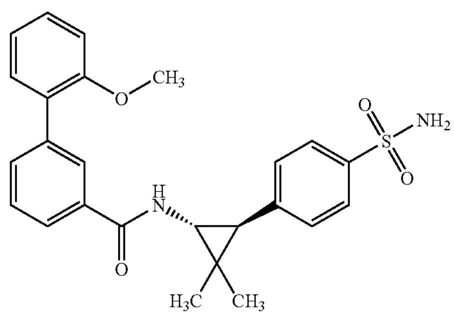 | 2'-Methoxy-biphenyl-3-carboxylic acid [trans-2,2-dimethyl-3-(4-sulfamoyl-phenyl)-cyclopropyl]-amide | 451 |
| 92 | 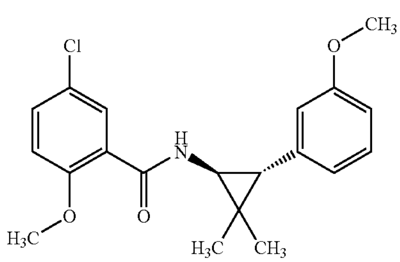 | 5-Chloro-2-methoxy-N-[trans-3-(3-methoxy-phenyl)-2,2-dimethyl-cyclopropyl]-benzamide | 360 |
| 93 | 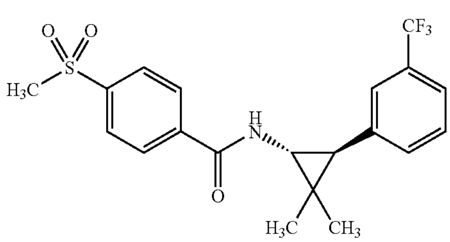 | N-[Trans-2,2-Dimethyl-3-(3-trifluoromethyl-phenyl)-cyclopropyl]-4-methanesulfonyl-benzamide | 412 |
| 94 | 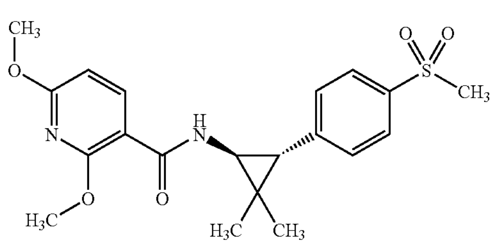 | N-[(1S,3R)-3-(4-Methanesulfonyl-phenyl)-2,2-dimethyl-cyclopropyl]-2,6-dimethoxy-nicotinamide | 405 |

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78 ° C. to about 150 ° C., more preferably from about 0 ° C. to about 125 ° C., and most preferably and conveniently at about room (or ambient) temperature, e.g., about 20 ° C.

Scheme A below illustrates one synthetic procedure usable to prepare compounds of the invention, wherein R is lower alkyl, X is hydroxy, halo or alkoxy, and $Ar^1$, $Ar^2$, $R^1$, and $R^2$ are as defined herein.

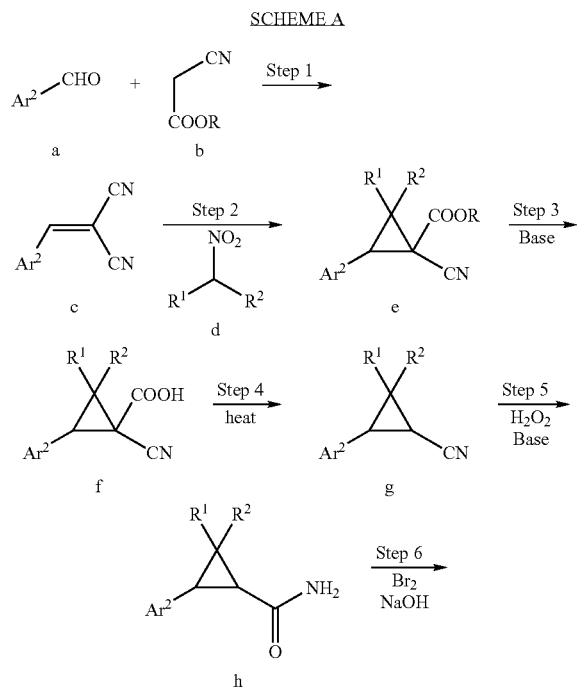

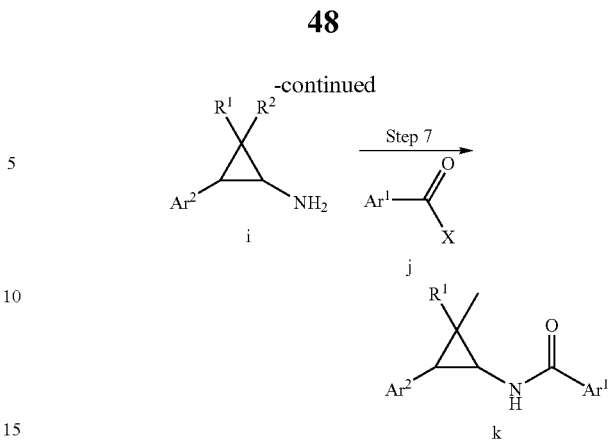

In Scheme A, aryl aldehyde compound a is reacted with cyano ester compound b to afford an arylonitrile ester compound c. This reaction may be carried out in the presence of amine base catalyst. Compound c is treated with nitro compound d step 2 to provide cyclopropyl nitrile ester compound e. In step 3 nitrile ester compound e is hydrolized under basic conditions to give cyclopropyl nitrile acid compound f In step 4 compound f is heated in the presence of base to afford cyclopropyl nitrile compound g. Nitrile compound g is then converted to cyclopropyl amide compound h in step 5 by treatment of compound g with hydrogen peroxide in the presence of base. In step 6 cyclopropyl amide compound is treated with bromine and NaOH or like base to afford cyclopropyl amine compound i. Amine compound i then undergoes an amide coupling reaction with acid compound j in step 7 to yield compound k, which is a compound of formula I in accordance with the invention.

Numerous variations on the procedures of Scheme A are possible and will be readily apparent to those skilled in the art. For example, nitrile compound g may be hydrolyzed directly to a carboxylic acid compound in step 5, and then treated with ethyl chloroformate followed by azide to form compound i. The amide formation of step 7 may utilize a carbodiimide such as dicyclohexylcarbodiimide, 1-(3-dimethylaminopropyl)-3-ethylcarbodiimide methiodide or other diimide as used in conventional amide coupling reactions. Desired stereochemistry may be introduced by selection of appropriate starting materials and/or use of chiral separation techniques. The amine compound i in many embodiments may undergo chromatographic chiral resolution to provide specific enantiomers.

Scheme B below illustrates another synthetic procedure for the compounds of the invention, wherein R is lower alkyl (preferably methyl), X is hydroxy, halo or alkoxy, and $Ar^1$, $Ar^2$, $R^1$, and $R^2$ are as defined herein.

SCHEME B

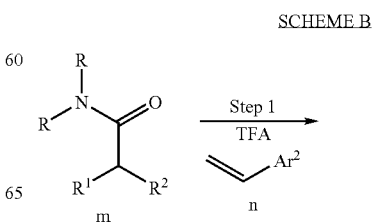

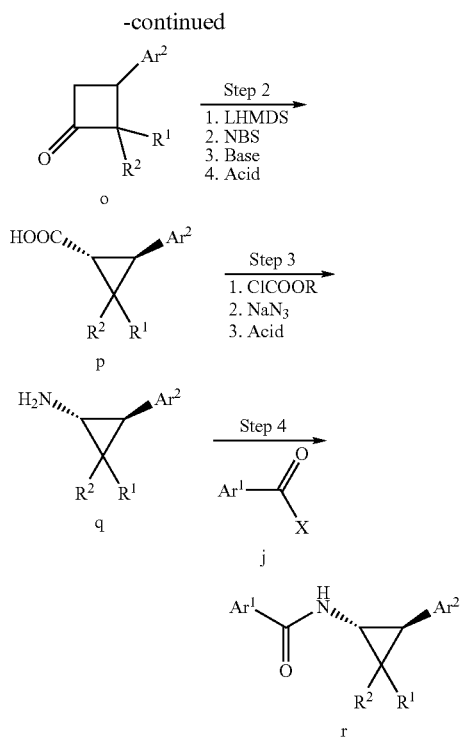

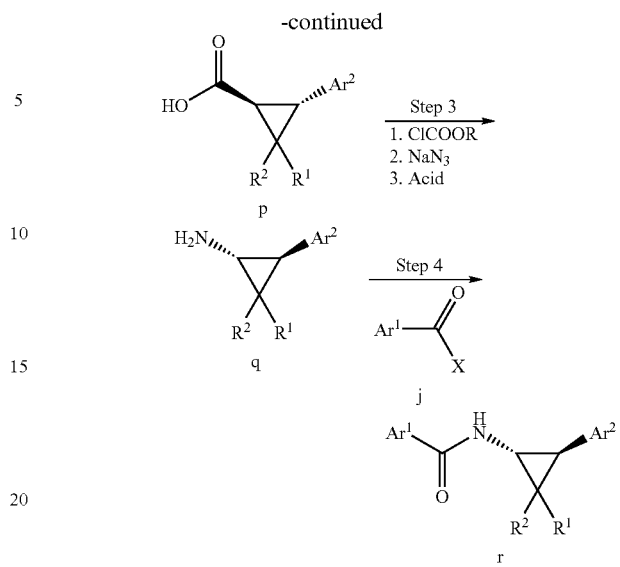

In step 1 of Scheme B, amide compound m is treated with trifluoroacetic anhydride, followed by styryl compound n, to afford cyclobutanone compound o. In step 2, cyclobutanone o is treated with Lithium bis(trimethylsilyl)amide, followed by n-bromo-succinimide or like brominating agent, then acid, and then base, to afford cyclopropyl acid compound p. Cyclopropyl compound p is converted to amine q in step 3 by treatment with chloroformate ester, followed by sodium azide and acidification. In step 4 cyclopropylamine q is subject to amide coupling with compound i to afford cyclopropyl amide r, which is a compound of formula I in accordance with the invention.

Scheme C shows yet another synthetic route to the compounds of the invention, wherein R is lower alkyl, and $Ar^1$, $Ar^2$, $R^1$, and $R^2$ are as defined herein.

SCHEME C

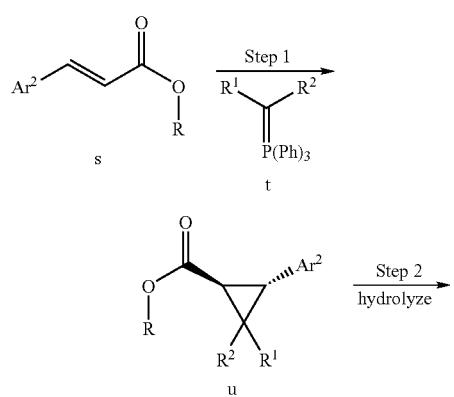

In step 1 of Scheme C, cinnamate ester compound s is reacted with Wittig reagent t to effect a cyclization reaction and provide cyclopyl ester compound u. Diazomethane may be used in place of Wittig reagent t to prepare compounds where $R^1$ and $R^2$ are hydrogen. Cyclopropyl ester u is hydrolized to cyclopropyl acid compound p. Compound p is then converted to an amine q in step 3 and undergoes amide coupling in step 4, following the same procedure of Scheme B, to afford cyclopropyl amide r.

Specific details for producing compounds of the invention are described in the Examples section below.

Utility

The compounds of the invention are usable for the treatment of diseases or conditions associated with the nicotinic alpha 7 (α7nACh) receptor, including treatment of psychotic diseases, neurodegenerative diseases, and cognitive impairments involving a dysfunction of the cholinergic system, and conditions of memory and/or cognition impairment, including, for example, schizophrenia, anxiety, mania, depression, manic depression, Tourette's syndrome, Parkinson's disease, Huntington's disease, cognitive disorders (such as Alzheimer's disease, Lewy Body Dementia, Amyotrophic Lateral Sclerosis, memory impairment, memory loss, cognition deficit, attention deficit, Attention Deficit Hyperactivity Disorder), and other uses such as treatment of nicotine addiction, inducing smoking cessation, treating pain (i.e., analgesic use), providing neuroprotection, and treating jetlag.

The compounds of the invention are useful for enhancing or improving cognition in Alzheimer's patients and patients having cognition impairment or cognitive disorders associated with schizophrenia, anxiety, mania, depression, manic depression, Tourette's syndrome, Parkinson's disease, Huntington's disease, Lewy Body Dementia, Amyotrophic Lateral Sclerosis, memory impairment, memory loss, cognition deficit, attention deficit or Attention Deficit Hyperactivity Disorder.

Thus, the invention provides a method of treating a patient or subject, specifically a mammal and especially a human, suffering from psychotic diseases, neurodegenerative diseases involving a dysfunction of the cholinergic system, and conditions of memory and/or cognition impairment, including, for example, schizophrenia, anxiety, mania, depression, manic depression [examples of psychotic disorders], Tourette's syndrome, Parkinson's disease, Huntington's disease [examples of neurodegenerative diseases], and/or cognitive disorders (such as Alzheimer's disease, Lewy Body Dementia, Amyotrophic Lateral Sclerosis, memory impairment, memory loss, cognition deficit, attention deficit, Attention Deficit Hyperactivity Disorder) comprising administering to the patient an effective amount of a compound of the invention.

Neurodegenerative disorders include, but are not limited to, treatment and/or prophylaxis of Alzheimer's diseases, Pick's disease, diffuse Lewy Body disease, progressive supranuclear palsy (Steel-Richardson syndrome), multisystem degeneration (Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3, olivopontocerebellar degenerations, Gilles De La Tourette's disease, bulbar, pseudobulbar palsy, spinal muscular atrophy, spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, prion diseases (such as Creutzfeldt-Jakob, Gerstmann-Sträussler-Scheinker disease, Kuru and fatal familial insomnia), and neurodegenerative disorders resulting from cerebral ischemia or infarction including embolic occlusion and thrombotic occlusion as well as intracranial hemorrhage of any type (including, but not limited to, epidural, subdural, subarachnoid and intracerebral), and intracranial and intravertebral lesions (including, but not limited to, contusion, penetration, shear, compression and laceration).

In addition, the compounds of the invention may be used to treat age-related dementia and other dementias and conditions with memory loss including age-related memory loss, senility, vascular dementia, diffuse white matter disease (Binswanger's disease), dementia of endocrine or metabolic origin, dementia of head trauma and diffuse brain damage, dementia pugilistica and frontal lobe dementia. Thus, the invention provides a method of treating a patient, especially a human, suffering from age-related dementia and other dementias and conditions with memory loss, as well as enhancing cognitive memory in Alzheimer's patients, comprising administering to the patient an effective amount of a compound of the invention.

The invention provides methods of treating subjects suffering from memory impairment due to, for example, Alzheimer's disease, mild cognitive impairment due to aging, schizophrenia, Parkinson's disease, Huntington's disease, Pick's disease, Creutzfeldt-Jakob disease, depression, aging, head trauma, stroke, CNS hypoxia, cerebral senility, multiinfarct dementia and other neurological conditions, as well as HIV and cardiovascular diseases, comprising administering an effective amount of a compound of the invention.

Amyloid precursor protein (APP) and Aβ peptides derived therefrom, e.g., $A\beta_{1-40}$, $A\beta_{1-42}$, and other fragments, are known to be involved in the pathology of Alzheimer's disease. The $A\beta_{1-42}$ peptides are not only implicated in neurotoxicity but also are known to inhibit cholinergic transmitter function. Further, it has been determined that Aβ peptides bind to α7nACh receptors. Agents which block the binding of the Aβ peptides to α-7 nAChRs are thus useful for treating neurodegenerative diseases. In addition, stimulation α7nACh receptors can protect neurons against cytotoxicity associated with Aβ peptides. Thus, the invention provides a method of treating and/or preventing dementia in an Alzheimer's patient which comprises administering to the subject a therapeutically effective amount of a compound according to Formulas I-IV to inhibit the binding of an amyloid beta peptide (preferably, $A\beta_{1-42}$) with nACh receptors, preferable α7nACh receptors, most preferably, human α7nACh receptors (as well as a method for treating and/or preventing other clinical manifestations of Alzheimer's disease that include, but are not limited to, cognitive and language deficits, apraxias, depression, delusions and other neuropsychiatric symptoms and signs, and movement and gait abnormalities).

The invention also provides methods for treating other amyloidosis diseases, for example, hereditary cerebral angiopathy, nonneuropathic hereditary amyloid, Down's syndrome, macroglobulinemia, secondary familial Mediterranean fever, Muckle-Wells syndrome, multiple myeloma, pancreatic- and cardiac-related amyloidosis, chronic hemodialysis anthropathy, and Finnish and Iowa amyloidosis.

Nicotinic receptors have been implicated as playing a role in the body's response to alcohol ingestion, and the compounds of the invention are useful in the treatment of alcohol withdrawal and in anti-intoxication therapy.

Agonists for the α7nACh receptor subtypes can also be used for neuroprotection against damage associated with strokes and ischemia and glutamate-induced excitotoxicity, and the invention thus provides a method of treating a patient to provide for neuroprotection against damage associated with strokes and ischemia and glutamate-induced excitotoxicity comprising administering to the patient an effective amount of a compound of the invention.

Agonists for the α7nACh receptor subtypes can also be used in the treatment of nicotine addiction, inducing smoking cessation, treating pain, and treating jetlag, obesity, diabetes, and inflammation, and the invention thus provides a method of treating a patient suffering from nicotine addiction, pain, jetlag, obesity, diabetes, and/or inflammation, or a method of inducing smoking cessation in a patient comprising administering to the patient an effective amount of a compound of the invention The inflammatory reflex is an autonomic nervous system response to an inflammatory signal. Upon sensing an inflammatory stimulus, the autonomic nervous system responds through the vagus nerve by releasing acetylcholine and activating nicotinic α7 receptors on macrophages. These macrophages in turn release cytokines. Dysfunctions in this pathway have been linked to human inflammatory diseases including rheumatoid arthritis, diabetes and sepsis. Macrophages express the nicotinic α7 receptor and it is likely this receptor that mediates the cholinergic anti-inflammatory response. Therefore, compounds of the invention may be useful for treating a patient (e.g., a mammal, such as a human) suffering from an inflammatory disease or disorder, such as, but not limited to, rheumatoid arthritis, diabetes or sepsis.

The compounds of the invention are expected to find utility as analgesics in the treatment of diseases and conditions associated with pain from a wide variety of causes, including, but not limited to, inflammatory pain, surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

Further, compounds of the invention are useful for treating respiratory disorders, including chronic obstructive pulmonary disorder (COPD), asthma, bronchospasm, and the like.

In addition, due to their affinity to α7nACh receptors, labeled derivatives of the compounds of Formulas I-IV (e.g., $C^{11}$ or $F^{18}$ labeled derivatives), can be used in neuroimaging of the receptors within, e.g., the brain. Thus, using such labeled agents in vivo imaging of the receptors can be performed using, e.g., PET imaging.

The invention also provides a method of treating a patient suffering from, for example, mild cognitive impairment (MCI), vascular dementia (VaD), age-associated cognitive decline (AACD), amnesia associated w/open-heart-surgery, cardiac arrest, and/or general anesthesia, memory deficits from early exposure of anesthetic agents, sleep deprivation induced cognitive impairment, chronic fatigue syndrome, narcolepsy, AIDS-related dementia, epilepsy-related cognitive impairment, Down's syndrome, Alcoholism related dementia, drug/substance induced memory impairments, Dementia Puglistica (Boxer Syndrome), and animal dementia (e.g., dogs, cats, horses, etc.) comprising administering to the patient an effective amount of a compound of the invention.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable. organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

EXAMPLES

The following preparations and examples are given to enable those skilled in the art to more clearly understand and to practice the present invention. They should not be considered as limiting the scope of the invention, but merely as being illustrative and representative thereof. The following abbreviations may be used in the Examples.

ABBREVIATIONS

DCM dichloromethane/methylene chloride
DMF N,N-dimethylformamide
DMAP 4-dimethylaminopyridine
EDC-MeI 1-(3-dimethylaminopropyl)-3-ethylcarbodiimide methiodide
EtOAc ethyl acetate
EtOH ethanol
tBuOH tert-butanol
gc gas chromatography
HMPA hexamethylphosphoramide
hplc high performance liquid chromatography
mCPBA m-chloroperbenzoic acid
MeCN acetonitrile
NMP N-methyl pyrrolidinone
TEA triethylamine
TFA trifluoroacetic acid
THF tetrahydrofuran
LDA lithium diisopropylamine
LHMDS Lithium bis(trimethylsilyl)amide TBAF tetrabutylammonium fluoride
TLC thin layer chromatography Preparation 1

2,2-Dimethyl-3-phenyl-cyclopropanecarbonitrile

The synthetic procedure described in this Preparation was carried out according to the process shown in Scheme D.

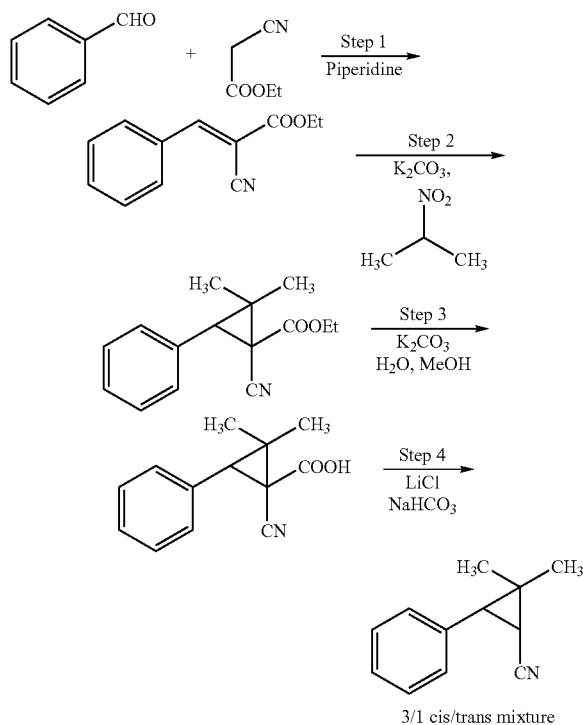

3/1 cis/trans mixture

Step 1 (E)-2-Cyano-3-phenyl-acrylic acid ethyl ester

A mixture of benzaldehyde (0.6 mol, 63.7 g), ethyl cyanoacetate (0.6 mol, 67.8 g) and piperidine (1 mL) in EtOH (60 mL) was stirred overnight. The clear solution was then placed in an ice-water bath to initiate the crystallization. The crystalline material was filtered, washed with EtOH and dried in a vacuum oven at 50° C. to give 58.27 g of (E)-2-cyano-3-phenyl-acrylic acid ethyl ester. The mother liquors and the washings were concentrated under reduced pressure; the residue was cooled in an ice-water bath to produce more crystalline product. This material was collected by filtration and washed with hexane, and a mixture EtOH/hexane (1/4), it was then dried in a vacuum oven at 63° C. to give 38.01 g of (E)-2-cyano-3-phenyl-acrylic acid ethyl ester (80% combined yield).

Step 2  1-Cyano-2,2-dimethyl-3-phenyl-cyclopropanecarboxylic acid ethyl ester

A mixture of (E)-2-cyano-3-phenyl-acrylic acid ethyl ester (83.6 g, 415 mmol), 2-nitropropane (37 g, 415 mmol) and potassium carbonate (57.4 g, 415 mmol) in EtOH (325 mL) was heated at reflux for 4 hours, then heated to 50° C. for 18 hours. The reaction mixture was then poured into an aqueous solution of NaCl (15%, 2 L) and extracted with DCM. The organic layer was separated, dried over $Na_2SO_4$, filtered, and evaporated under reduced pressure. The residue was purified by distillation under vacuum to give 1-cyano-2,2-dimethyl-3-phenyl-cyclopropanecarboxylic acid ethyl ester (64.26 g, 64% yield, pale yellow oil) which distilled at 118° C. (oil bath temperature 157° C.).

Step 3  1-Cyano-2,2-dimethyl-3-phenyl-cyclopropanecarboxylic acid

A solution of potassium carbonate (40 g) in water (125 mL) was added to a solution of 1-cyano-2,2-dimethyl-3-phenyl-cyclopropanecarboxylic acid ethyl ester (64.26 g, 264 mmol) in MeOH (500 mL). The reaction mixture was heated at reflux for 1 hour and then stirred overnight at 85° C. The volatiles where evaporated under reduced pressure, and the residue was diluted with water and washed twice with EtOAc. The phases were separated and the aqueous phase was acidified by addition of HCl (concentrated). Ethyl ether was added and the mixture was carefully extracted. The organic layer was separated, dried over $Na_2SO_4$, filtered and evaporated under reduced pressure to give 27.2 g (49% yield) of 1-cyano-2,2-dimethyl-3-phenyl-cyclopropanecarboxylic acid as an off-white solid.

Step 4  2,2-Dimethyl-3-phenyl-cyclopropanecarbonitrile

To a solution of 1-cyano-2,2-dimethyl-3-phenyl-cyclopropanecarboxylic acid (13.6 g, 63 mmol) in DMSO (125 mL) was added LiCl (10.72 g, 252 mmol) followed by $NaHCO_3$ (7.96 g, 94.5 mmol) and water (4.55 g, 252 mmol). Gas evolution was observed, and within 30 minutes enough solids were dissolved to allow the milky mixture to stir. The reaction mixture was stirred at 170° C. for 18 hours, then cooled and poured into a mixture of water and brine (7/1, 800 mL) and extracted with ethyl ether. The combined organic extracts were dried over $Na_2SO_4$, filtered and evaporated under reduced pressure to give 7.79 g (76% yield) of 2,2-dimethyl-3-phenyl-cyclopropanecarbonitrile (3/1, cis/trans mixture).

Preparation 2

Trans-2,2-Dimethyl-3-phenyl-cyclopropylamine

The synthetic procedure described in this Preparation was carried out according to the process shown in Scheme E.

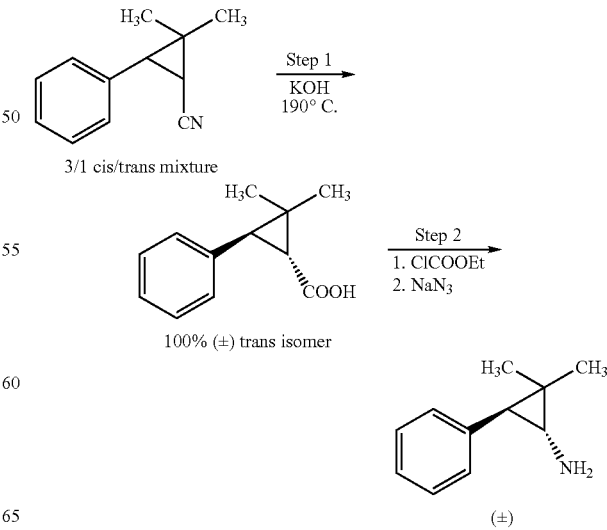

Step 1

Trans-2,2-Dimethyl-3-phenyl-cyclopropanecarboxylic acid

A mixture of 2,2-dimethyl-3-phenyl-cyclopropanecarbonitrile (cis/trans mixture, 3.2 g, 18.7 mmol) and freshly ground KOH (3.143 g, 56.1 mmol) in ethylene glycol was heated at 165° C. for 28 hours. The reaction mixture was then cooled and poured into a mixture of water and brine (300 mL). The resulting mixture was extracted 3 times with ethyl ether, the combined organic extracts were dried over $Na_2SO_4$, filtered and evaporated under reduced pressure to give 3.36 g (95% yield) of trans-2,2-dimethyl-3-phenyl-cyclopropanecarboxylic acid.

Step 2

Trans-2,2-Dimethyl-3-phenyl-cyclopropylamine

To a solution of trans-2,2-dimethyl-3-phenyl-cyclopropanecarboxylic acid (1.78 g, 9.4 mmol) in acetone was added water (4 mL) followed, at −5° C., by ethyl chloroformate (0.982 mL, 10.34 mmol). The reaction mixture was stirred for 20 minutes and then a solution of sodium azide (731 mg, 11.28 mmol) in water (8 mL) was added. The resulting mixture was stirred for 45 minutes and then diluted with a 1:1 mixture of water and toluene. The organic layer was separated, dried over $Na_2SO_4$, filtered and heated at 100° C. for 1 hour. The solvent was then removed under reduced pressure and an aqueous solution of HCl (8 M, 30 mL) was added, and the resulting mixture was heated at reflux for 45 minutes. The reaction mixture was cooled and an aqueous solution of HCl (10%) was added; the resulting mixture was washed with ethyl ether, then basified by addition of NaOH. The resulting mixture was extracted with ethyl ether, and the combined organic extracts were dried over $Na_2SO_4$, filtered, and evaporated under reduced pressure to give 1.05 g (70% yield) of trans-2,2-dimethyl-3-phenyl-cyclopropylamine.

Utilizing the procedure above described and the appropriate starting material, trans-2,2-dimethyl-3-(4-trifluoromethyl-phenyl)-cyclopropylamine was prepared.

Preparation 3

Cis-2,2-Dimethyl-3-phenyl-cyclopropylamine

The synthetic procedure described in this Preparation was carried out according to the process shown in Scheme F.

SCHEME F

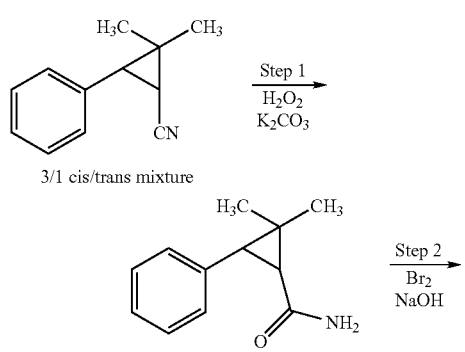

3/1 cis/trans mixture

-continued

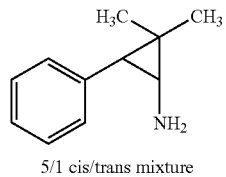

5/1 cis/trans mixture

Step 1

2,2-Dimethyl-3-phenyl-cyclopropanecarboxylic acid amide

Potassium carbonate (467 mg) was added to a solution of 2,2-dimethyl-3-phenyl-cyclopropanecarbonitrile (3/1 cis/trans mixture, 4 g, 23.4 mmol) in DMSO (7 mL). The resulting mixture was cooled to 0° C. and an aqueous solution of hydrogen peroxide (30%, 2.8 mL) was added. The reaction mixture was allowed to warm up to room temperature and was stirred overnight. A second aliquot of aqueous solution of hydrogen peroxide (30%, 2.8 mL) was added and the resulting mixture was stirred for 24 hours. A third aliquot of aqueous solution of hydrogen peroxide (30%, 3.0 mL) was added and the resulting mixture was stirred for 3 days. The reaction mixture was poured into brine and extracted with ethyl ether. The organic layer was separated, dried over $Na_2SO_4$, filtered, and evaporated under reduced pressure. The crude residue was purified by flash chromatography (0% to 65% of EtOAc in hexane) to give 2.66 of 2,2-dimethyl-3-phenyl-cyclopropanecarboxylic acid amide (2/1 trans/cis mixture), together with 1.125 g of starting material.

Step 2

Cis-2,2-Dimethyl-3-phenyl-cyclopropylamine

Bromine (2.2 mL, 42.4 mmol) was added to an aqueous solution of NaOH (10%) at 0° C. The mixture was stirred vigorously, then added to a flask containing cis-2,2-dimethyl-3-phenyl-cyclopropanecarboxylic acid amide (2.01 g, 10.6 mmol) at 0° C. The reaction mixture was heated to 85° C. for 3 hours, then cooled and poured into a mixture of water and brine. The resulting mixture was extracted with ethyl ether, and the combined organic extracts were washed twice with an aqueous solution of HCl (10%). The aqueous layer was basified and extracted with ethyl ether. The combined organic extracts were dried over $Na_2SO_4$, filtered, and evaporated under reduced pressure to give 600 mg of 2,2-dimethyl-3-phenyl-cyclopropylamine cis/trans 5/1.

Preparation 4

Trans-2,2-Dimethyl-3-p-tolyl-cyclopropylamine

The synthetic procedure described in this Preparation was carried out according to the process shown in Scheme G.

SCHEME G

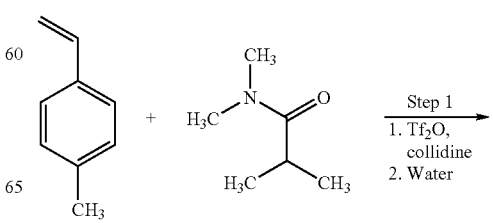

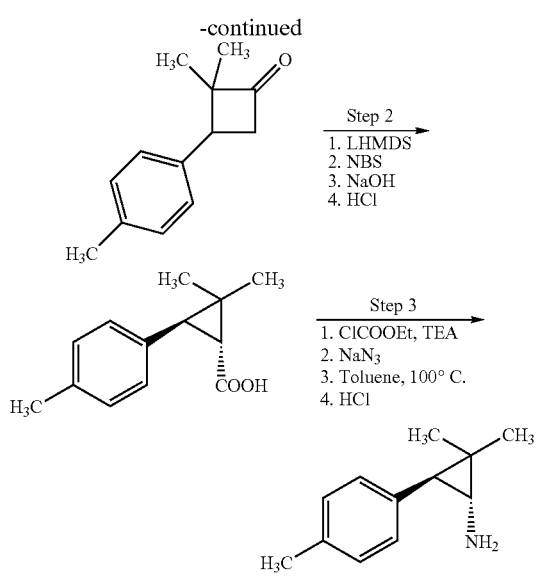

Step 1

2,2-Dimethyl-3-p-tolyl-cyclobutanone

Trifluoroacetic anhydride (25 g, 0.09 mol) was added portionwise over a period of 10 minutes at −10° C., to a solution of N,N-dimethyl-isobutyramide (9.16 g) in DCM (100 mL). The resulting mixture was stirred at −10° C. for 10 minutes and then a viscous solution of 4-methylstyrene (8.2 g) and collidine (11.9 mL) in DCM (15 mL) was added portionwise at −10° C. The resulting mixture was heated at reflux for 22 hours then cooled and concentrated under reduced pressure. The oil residue was washed with ethyl ether and the organic phase was decanted away. DCM (75 mL) and water (75 mL) were added to the oil and the mixture was heated at 100° C. for 6 hours. The mixture was cooled to room temperature, separated, and the aqueous layer was extracted with DCM. The combined organic extracts were dried over $Na_2SO_4$, filtered, and evaporated under reduced pressure to give 35 g of crude oil, which was purified by flash chromatography (5% to 50% of EtOAc in hexane) to give 6.45 g (50% yield) of 2,2-dimethyl-3-p-tolyl-cyclobutanone as a yellow oil.

Step 2

Trans-2,2-Dimethyl-3-p-tolyl-cyclopropanecarboxylic acid

A solution of lithium bis(trimethylsilyl)amide (1.0 M in THF, 38 mL) was added dropwise over a period of 20 minutes at −78° C. to a solution of 2,2-dimethyl-3-p-tolyl-cyclobutanone (6.4 g, 34 mmol) in THF (340 mL). The reaction mixture was stirred at −78° C. for 30 minutes and the resulting yellow solution was stirred at 0° C. for 15 minutes; it was then cooled again at −78° C. and a solution of N-bromosuccinimide (6.6 g) in THF (85 mL) was added dropwise. The resulting suspension was stirred at 0° C. for 30 minutes, and a solution of NaOH (8.43 g) in water (85 mL) was then added. The reaction mixture was allowed to warm up to room temperature and was stirred for 1 hour. Volatiles were then evaporated under reduced pressure. The aqueous residue was extracted with ethyl ether and the combined organic extracts were dried over $Na_2SO_4$, filtered, and evaporated under reduced pressure to give 4.2 g of staring material. The aqueous layer was diluted with water and acidified until pH 1. by addition of concentrated HCl (25 mL). The resulting mixture was stored in at 4° C. for 2 days, during which time a yellow solid precipitated. This material was collected by filtration, washed with cold water and dried to give 3 g (40% yield) of trans-2,2-dimethyl-3-p-tolyl-cyclopropanecarboxylic acid a yellow solid.

Step 3

Trans-2,2-Dimethyl-3-p-tolyl-cyclopropylamine

Ethyl chloroformate (1.2 mL) was added to a solution of trans-2,2-dimethyl-3-p-tolyl-cyclopropanecarboxylic acid (2.3 g, 11 mmol) and triethylamine (1.7 mL) in a mixture of acetone (15 mL) and water (2.9 mL). The reaction mixture was stirred for 20 minutes, then a solution of sodium azide (0.81 g) in water (5.8 mL) was added and the resulting mixture was stirred for 45 minutes. The reaction mixture was partitioned between water and toluene (1/1 mixture, 50 mL), and the organic layer was separated, dried over $Na_2SO_4$ and filtered. The organic layer was heated at 100° C., then cooled and evaporated under high vacuum to give a tan oil. To this oil was added an aqueous solution of HCl (10 M, 30 mL), and the resulting mixture was heated at 100° C. The reaction mixture was allowed to cool to room temperature and was extracted with ethyl ether. The combined organic layers were dried over $Na_2SO_4$, filtered, and evaporated under reduced pressure to give 1.6 g of acid starting material. The aqueous layer was basified by addition of an aqueous solution of NaOH, then extracted with DCM. The organic layer was separated, dried over $Na_2SO_4$, filtered, and evaporated under reduced pressure to give 510 mg of trans-2,2-dimethyl-3-p-tolyl-cyclopropylamine as a brown oil.

Example 1

5-Chloro-N-(trans-2,2-dimethyl-3-phenyl-cyclopropyl)-2-methoxy-benzamide

The synthetic procedure described in this Example was carried out according to the process shown in Scheme H.

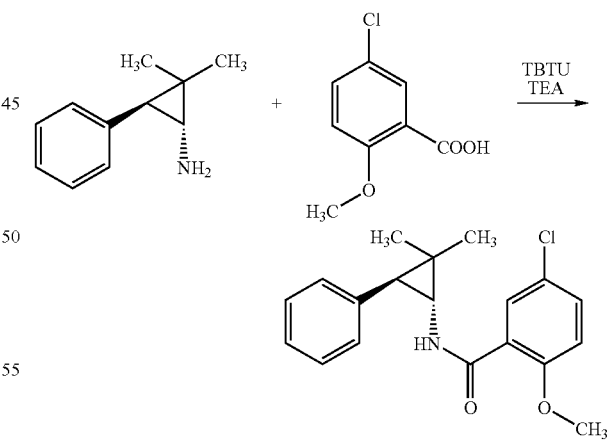

To a solution of trans-2,2-dimethyl-3-phenyl-cyclopropylamine (1.04 g, 6.5 mmol) in DCM was added triethylamine (1.435 g, 14.3 mmol), followed by 5-chloro-2-methoxybenzoic acid (1.446 g, 7.44 mmol) and O-benzotriazol-1-yl-N, N,N',N'-tetramethyluronium tetrafluoroborate (2.696 g, 8.45 mmol). The resulting mixture was stirred at room temperature overnight, then poured into water and extracted with DCM. The combined organic extracts were dried over $Na_2SO_4$, filtered, and evaporated under reduced pressure. The crude residue was purified by flash chromatography (0% to 15% of EtOAc in hexane) to give 1.71 g (86% yield) of trans-5-chloro-N-(2,2-dimethyl-3-phenyl-cyclopropyl)-2-methoxy-benzamide, MS=330 [M+H]$^+$.

In a similar manner, using the appropriate starting material, the following compounds were prepared:

Cis-5-Chloro-N-(2,2-dimethyl-3-phenyl-cyclopropyl)-2-methoxy-benzamide, MS=330 [M+H]$^+$;

Trans-5-Chloro-N-[2,2-dimethyl-3-(4-trifluoromethyl-phenyl)-cyclopropyl]-2-methoxy-benzamide, MS=398 [M+H]$^+$; and Trans-5-Chloro-N-[2,2-dimethyl-3-(4-trifluoromethyl-phenyl)-cyclopropyl]-2,4-dimethoxy-benzamide, MS=428 [M+H]$^+$.

Additional compounds prepared using the above procedure are shown in Table 1.

Example 2

5-Chloro-N-[Trans-2,2-dimethyl-3-(4-sulfamoyl-phenyl)-cyclopropyl]-2-methoxy-benzamide The synthetic procedure described in this Example was carried out according to the process shown in Scheme I.

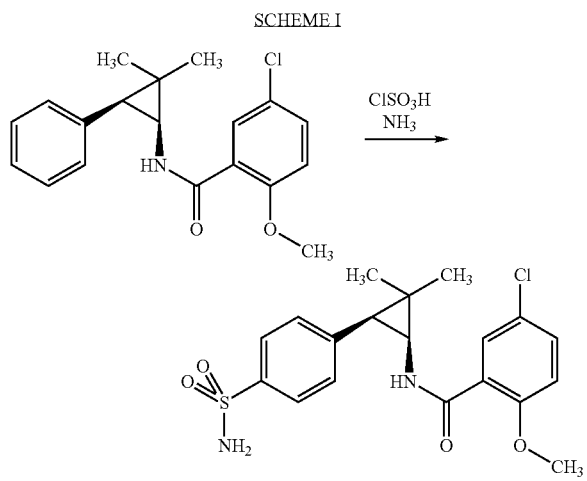

Chlorosulfonic acid (0.4 mL) was added dropwise to a solution of cis-5-chloro-N-(2,2-dimethyl-3-phenyl-cyclopropyl)-2-methoxy-benzamide (119 mg, 0.362 mmol) in chloroform. The reaction mixture was stirred for 30 minutes, then poured into a water/ice/brine mixture and extracted with ethyl ether. The combined organic extracts were dried over Na$_2$SO$_4$, filtered, and evaporated under reduced pressure. The residue was dissolved in 1,4-dioxane and NH$_4$OH (concentrated) was added. The resulting mixture was stirred for 45 minutes, then poured into a mixture of water and brine and extracted with EtOAc. The combined organic extracts were dried over Na$_2$SO$_4$, filtered, and evaporated under reduced pressure. The crude residue was recrystallized from DCM to give 10 mg of cis-5-chloro-N-[2,2-dimethyl-3-(4-sulfamoyl-phenyl)-cyclopropyl]-2-methoxy-benzamide. The mother liquors were evaporated under reduced pressure to give a mixture of cis and trans products. MS=409 [M+H]$^+$.

In a similar manner, using the appropriate starting materials, the following compounds were prepared:

Cis-5-Chloro-N-[3-(4-dimethylsulfamoyl-phenyl)-2,2-dimethyl-cyclopropyl]-2-methoxy-benzamide, MS=437 [M+H]$^+$; and Trans-5-Chloro-N-[2,2-dimethyl-3-(4-sulfamoyl-phenyl)-cyclopropyl]-2-methoxy-benzamide, MS=409 [M+H]$^+$.

Additional compounds prepared using the above procedure are shown in Table 1.

Example 3

5-Chloro-N-(trans-2,2-dimethyl-3-p-tolyl-cyclopropyl)-2-methoxy-benzamide

The synthetic procedure described in this Example was carried out according to the process shown in Scheme J.

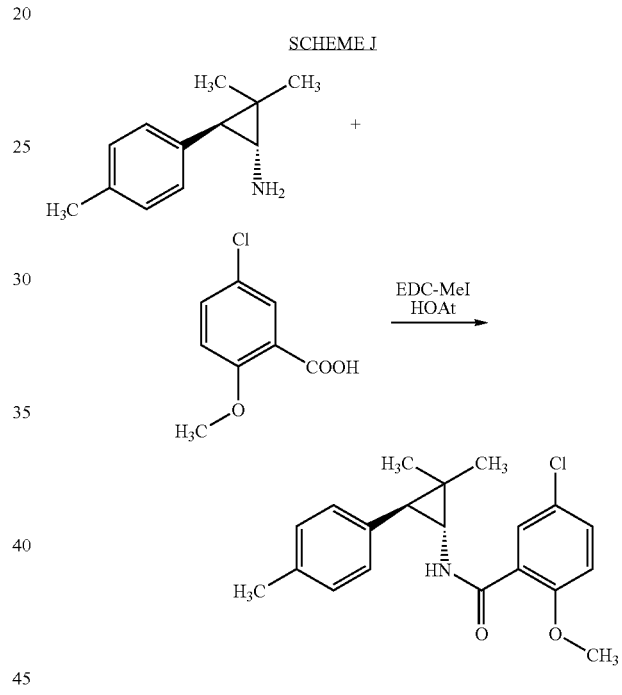

1-(3-Dimethylaminopropyl)-3-ethylcarbodiimide methiodide (130 mg) was added at 0° C. to a mixture of Trans-2,2-dimethyl-3-p-tolyl-cyclopropylamine (70 mg, 0.4 mmol), 5-chloro-2-methoxybenzoic acid (75 mg), and 1-hydroxy-7-azabenzotriazole (107 mg) in DCM (2 mL). The reaction mixture was stirred at 0° C. for 30 minutes, then allowed to warm to room temperature. The mixture was partitioned between an aqueous solution of HCl (1 M) and DCM. The combined organic extracts were washed with a saturated aqueous solution of NaHCO$_3$, dried over Na$_2$SO$_4$, filtered, and evaporated under reduced pressure to give 160 mg of a tan foam. This crude residue was purified by flash chromatography (0% to 100% Et$_2$O in hexane) to give 70 mg of 5-chloro-N-(trans-2,2-dimethyl-3-p-tolyl-cyclopropyl)-2-methoxy-benzamide, MS=344 [M+H]$^+$.

In a similar manner, utilizing the appropriate starting material, 5-chloro-N-(trans-2,2-dimethyl-3-p-tolyl-cyclopropyl)-2,4-dimethoxy-benzamide was prepared; MS=374 [M+H]$^+$; MP=148.3-150.9° C.

Additional compounds prepared using the above procedure are shown in Table 1.

Example 4

N-(Trans-2,2-Dimethyl-3-p-tolyl-cyclopropyl)-benzamide

The synthetic procedure described in this Example was carried out according to the process shown in Scheme K.

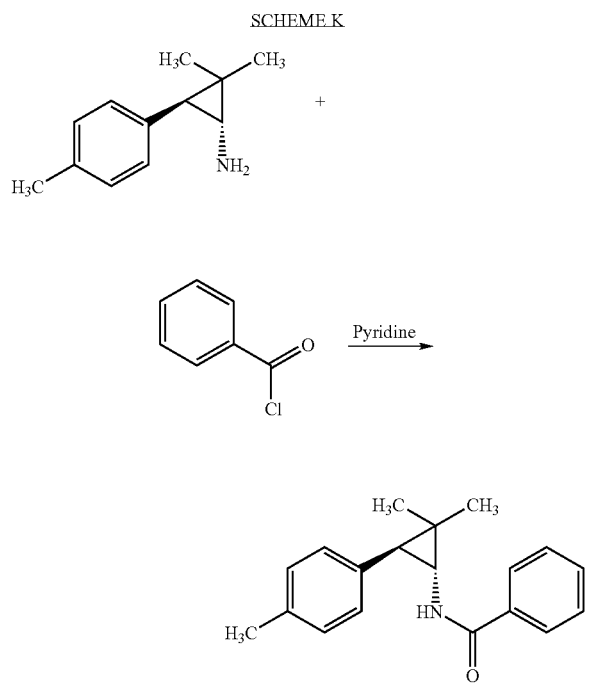

Benzoyl chloride (37 µL) was added at 0° C. to a solution of trans-2,2-dimethyl-3-p-tolyl-cyclopropylamine (50 mg, 0.28 mmol) in pyridine (1 mL). The reaction mixture was slowly allowed to warm up to room temperature, then was partitioned between an aqueous solution of HCl (1 M) and DCM. The combined organic extracts were washed with a saturated aqueous solution of NaHCO$_3$, dried over Na$_2$SO$_4$, filtered, and evaporated under reduced pressure to give 50 mg of a tan oil which was purified by preparative HPLC. A Zorbax 3.5 um, 4.6×50 mm SB-phenyl column was used with solvent A (water with 0.1% (V/V) formic acid) and solvent B (acetonitrile), A/B 75/25 from 0 to 1 minute, A/B 5/95 at 6 minutes, A/B 75/25 at 6.5 minutes, A/B 75/25 at 7.0 minutes, flow rate 1.0 mL/minute. MS=280 [M+H]$^+$.

In a similar manner, utilizing the appropriate starting material, N-(trans-2,2-dimethyl-3-p-tolyl-cyclopropyl)-4-methyl-benzamide was prepared, MS=294 [M+H]$^+$.

Additional compounds prepared using the above procedure are shown in Table 1.

Example 5

5-Chloro-N-[Trans-3-(4-methanesulfonyl-phenyl)-2,2-dimethyl-cyclopropyl]-2-methoxy-benzamide The synthetic procedure described in this Example was carried out according to the process shown in Scheme L.

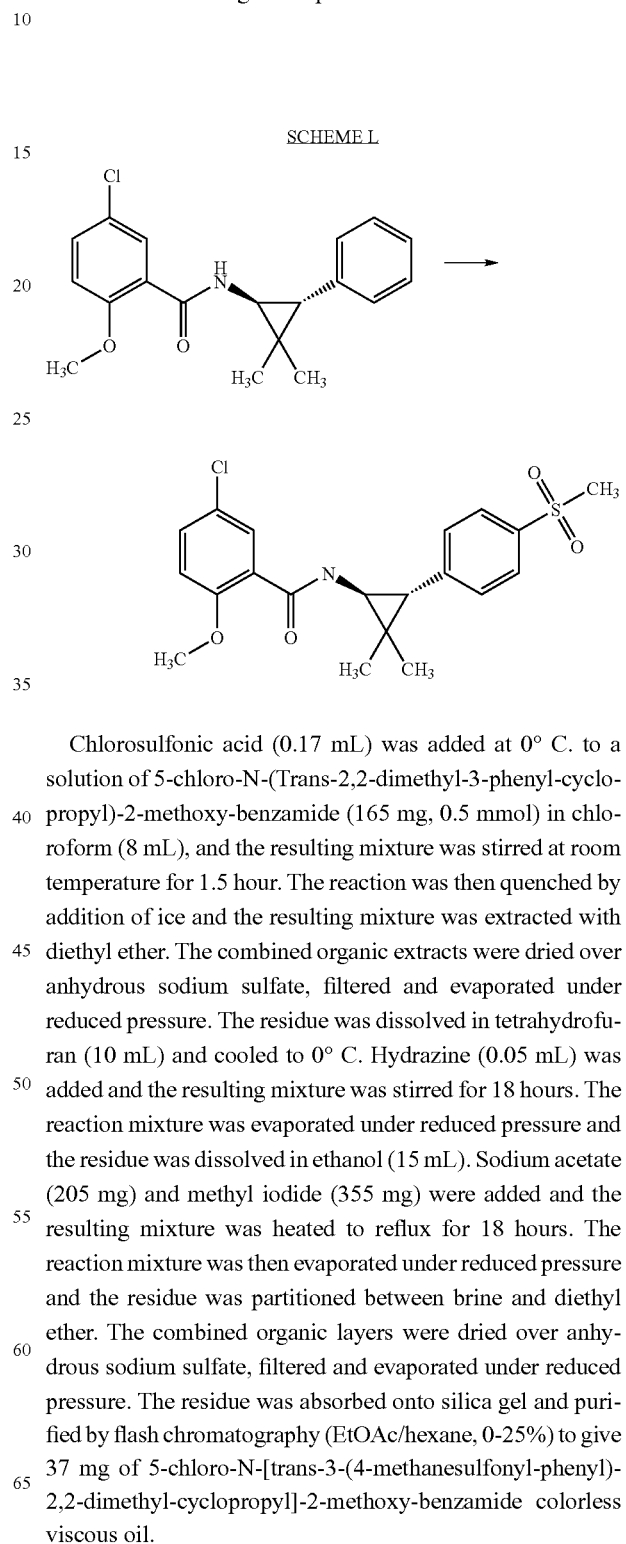

Chlorosulfonic acid (0.17 mL) was added at 0° C. to a solution of 5-chloro-N-(Trans-2,2-dimethyl-3-phenyl-cyclopropyl)-2-methoxy-benzamide (165 mg, 0.5 mmol) in chloroform (8 mL), and the resulting mixture was stirred at room temperature for 1.5 hour. The reaction was then quenched by addition of ice and the resulting mixture was extracted with diethyl ether. The combined organic extracts were dried over anhydrous sodium sulfate, filtered and evaporated under reduced pressure. The residue was dissolved in tetrahydrofuran (10 mL) and cooled to 0° C. Hydrazine (0.05 mL) was added and the resulting mixture was stirred for 18 hours. The reaction mixture was evaporated under reduced pressure and the residue was dissolved in ethanol (15 mL). Sodium acetate (205 mg) and methyl iodide (355 mg) were added and the resulting mixture was heated to reflux for 18 hours. The reaction mixture was then evaporated under reduced pressure and the residue was partitioned between brine and diethyl ether. The combined organic layers were dried over anhydrous sodium sulfate, filtered and evaporated under reduced pressure. The residue was absorbed onto silica gel and purified by flash chromatography (EtOAc/hexane, 0-25%) to give 37 mg of 5-chloro-N-[trans-3-(4-methanesulfonyl-phenyl)-2,2-dimethyl-cyclopropyl]-2-methoxy-benzamide colorless viscous oil.

Example 6

Chiral Separation and Absolute Configuration Determination of 5-Chloro-N-[(1S,3R)-2,2-dimethyl-3-(4-sulfamoyl-phenyl)-cyclopropyl]-2-methoxy-benzamide and 5-Chloro-N-[(1R,3S)-2,2-dimethyl-3-(4-sulfamoyl-phenyl)-cyclopropyl]-2-methoxy-benzamide

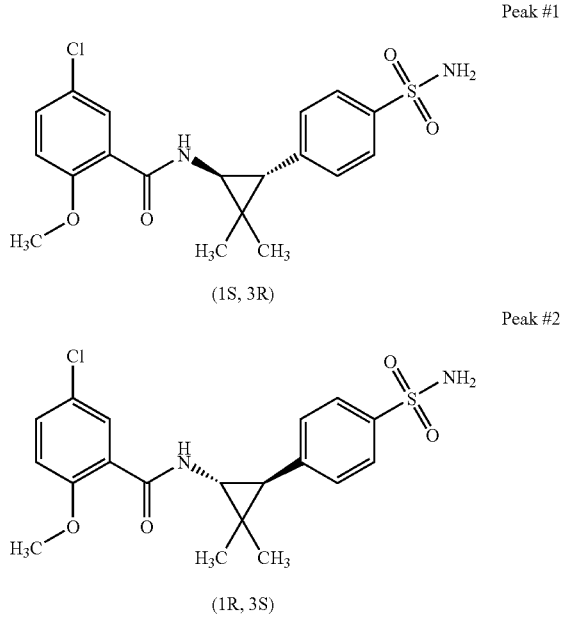

Trans-5-Chloro-N-[2,2-dimethyl-3-(4-sulfamoyl-phenyl)-cyclopropyl]-2-methoxy-benzamide was purified by preparative chiral HPLC through multiple injections on a Chiralpak AD preparative column (20 mm ID by 250 mm length, 10 micron packing) using 100% EtOH at 6 ml/min over 30 minutes to give the two enantiomers:

Peak #1 retention time 8.9 minutes (−)-enantiomer 883 mg; and

Peak #2 retention time 16.9 minutes (+)-enantiomer 875 mg.

These two samples were recrystallized separately. The (−)-enantiomer was recrystallized from EtOH (7 mL), and the solid was dried overnight over $P_2O_5$ at 55° C. This material was then re-dissolved in EtOAc and evaporated under reduced pressure three times. The resulting material was then dissolved in DCM and evaporated under reduced pressure four times. The material thus obtained was dried overnight in a drying pistol over refluxing acetone under reduced pressure to give 634.5 mg of a foam, MP=96.3-102.1° C., $\alpha_D$=−109.7° (c=0.518, MeOH).

The (+)-Enantiomer (875 mg) was dissolved in DCM and evaporated under reduced pressure at 60° C. three times. The resulting solid was dissolved in DCM and hexane was added. The resulting solution was evaporated under reduced pressure at 65° C., and this operation was repeated three times to give a foam that was dried under high vacuum overnight. A portion of this material (182 mg) was recrystallized from 2-propanol to give crystals containing one mole of 2-propanol per mole of solvate. The crystal structure of this material was solved by X-ray diffraction and it allowed the determination of the absolute 1R, 3S configuration shown above, $\alpha_D$=+86.2° (c=, MeOH).

Example 7

5-Chloro-2-methoxy-N-[trans-3-(3-methoxy-phenyl)-2,2-dimethyl-cyclopropyl]-benzamide The synthetic procedure described in this Example was carried out according to the process shown in Scheme M.

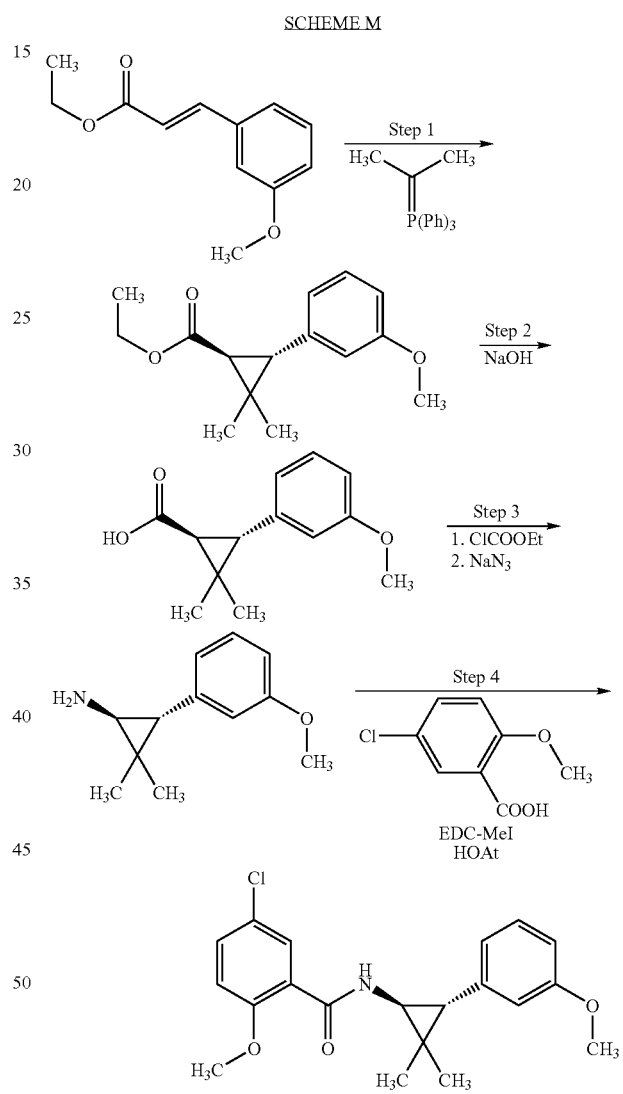

Step 1 Trans-3-(3-Methoxy-phenyl)-2,2-dimethyl-cyclopropanecarboxylic acid ethyl ester Cyclopropanation of 3-methoxy-cinnamic acid methyl ester was carried out following the procedure of Ahmand et al., *J Med. Chem* 2001, 44, 3302-3310. Isopropyl-triphenylphosphonium iodide was prepared as described by Grieco et al., *Tet. Lett.* 1972, 36, 3781-3783. Briefly, a solution of 3-methoxy-cinnamic acid ethyl ester (14.6 g, 70.9 mmol) in 300 mL THF was cooled in a dry ice/acetone bath to approximately −78° C., and added dropwise to a −78° C. stirring solution of isopropyl-triphenylphosphonium iodide (51 g. 118 mmol) and n-butyl-lithium (54 mL, 135 mmol) in THF. The reaction mixture was allowed to warm to 0° C. with stirring for two hours, then was stirred at room temperature for 15 hours. The reaction mixture was poured onto ice and the resulting aqueous mixture was adjusted to neutral pH by addition of 1M aqueous $H_2SO_4$. The aqueous solution was extracted three times with a 1/1 mixture of hexanes/EtOAc and once with EtOAc. The combined organic layers were filtered through silica, and the filtrate was dried over $MgSO_4$, filtered, and concentrated under reduced pressure to give 15.22 g of crude trans-3-(3-methoxy-phenyl)-2,2-dimethyl-cyclopropanecarboxylic acid ethyl ester.

Step 2 Trans-3-(3-Methoxy-phenyl)-2,2-dimethyl-cyclopropanecarboxylic acid

Trans-3-(3-Methoxy-phenyl)-2,2-dimethyl-cyclopropanecarboxylic acid ethyl ester (15.22 g, 61 mmol) was added to a mixture of EtOH (200 mL) and 2M aqueous NaOH (100 mL). Solid NaOH (5.0 g, 125 mmol) was added, and the reaction mixture was stirred under $N_2$ atmosphere for 15 hours at room temperature. The reaction mixture was diluted with water and extracted twice with a mixture of 1/1 hexanes/diethyl ether and once with EtOAc. The combined organic layers were dried ($MgSO_4$), filtered, and concentrated under reduced pressure to give 11.5 g of trans-3-(3-methoxy-phenyl)-2,2-dimethyl-cyclopropanecarboxylic acid, MS=221 $[M+H]^+$.

Step 3 Trans-3-(3-Methoxy-phenyl)-2,2-dimethyl-cyclopropylamine

Trans-3-(3-Methoxy-phenyl)-2,2-dimethyl-cyclopropylamine was prepared from Trans-3-(3-methoxy-phenyl)-2,2-dimethyl-cyclopropanecarboxylic acid following the procedure of step 3 of Preparation 4 above, MS=$[M+H]^+$.

Step 4 5-Chloro-2-methoxy-N-[(Trans-3-(3-methoxy-phenyl)-2,2-dimethyl-cyclopropyl]-benzamide 5-Chloro-2-methoxy-N-[trans-3-(3-methoxy-phenyl)-2,2-dimethyl-cyclopropyl]-benzamide was prepared by reaction of (trans-3-(3-Methoxy-phenyl)-2,2-dimethyl-cyclopropylamine with 3-chloro-5-methoxy-benzoic acid following the procedure of Example 3, MS=360 $[M+H]^+$.

Example 8

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | grams |
|---|---|
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 9

Nicotinic Alpha 7 Modulation Assay

Cell Cultures

Cell Culture Growth Media: F10 medium (Invitrogen), 2.5% Fetal Bovine Serum (FBS, Summit Biotechnology); 15% heat inactivated donor Horse Serum (Invitrogen), 250 μg/ml Hygromycin B (Invitrogen); and 100 nM Methyllicaconite (MLA, Sigma) are added to each new culture by 50-fold dilution of stock solution prepared in $H_2O$ at 5 μM.

$GH_4C_1$ cells (rat pituitary-derived cell line) stably expressing human nicotinic alpha7 WT receptor (RPA clone #34.7) are cultivated in cell culture growth media (described above) at 37 C in a humidified atmosphere containing 4% $CO_2$. Fresh cell stock cultures are initiated with cells at $0.1-0.2 \times 10^6$/ml, 50 ml media per T225 flask and are grown for 2 or 3 day prior to use in FLIPR assay. Cells harvested two days after intiation of stock flask typically yields ~$25 \times 10^6$/T225 flask and 3 days after intiation of stock flask typically yields ~$40 \times 10^6$/T225 flask.

One day prior to assay, cells are placed in fresh cell culture growth media supplemented with 100 nM fresh MLA. To accomplish media change, suspension cells of the culture are removed and 45 ml fresh cell culture growth media (containing 100 nM fresh MLA) is immediately added to the stock flask as large numbers of cells remain adherent to the surface. The cells in suspension are then collected by centrifugation, resuspended in 5 ml fresh cell culture growth media and returned to the original culture flask.

Buffer Solutions

Buffer solutions used in the assay are HBSS FLIPR buffer (Invitrogen), 2 mM $CaCl_2$ (Sigma), 10 mM HEPES (Invitrogen), 2.5 mM Probenecid (Sigma), and 0.1% BSA (Sigma)

FLIPR Assay

The alpha 7 nAChR assay is a cell-based functional readout designed to determine the effect of test compounds to either directly activate nicotinic receptor channels and/or to modulate activation by the native agonist acetylcholine (ACh, Sigma).

On day one of the assay, attached cells are lifted using 1×-concentration Versene (Gibco, Cat-No. 15040), combined with cells in suspension, and collected by centrifugation (5 min, 162×g). The cell pellet is resuspended in FLIPR buffer at $0.5 \times 10^6$/ml and cells dispensed into sample wells of a 96-well poly-d-lysine coated black/clear plate (Becton Dickinson) at $0.5 \times 10^5$ cells per well. Sample wells are then supplemented with FLUO-3AM dye (TefLabs, stock solution prepared at 2.5 mM in anhydrous DMSO containing 10% Pluronic acid) in FLIPR buffer at 1 μM final assay concentration (FAC). Dye loading of cells occurs by incubation of plates for one hour at 37 C in a humidified atmosphere containing 4% $CO_2$. To remove extracellular dye, FLIPR plates are washed using a Biotek EL405 plate washer leaving a residual volume of 0.1 ml FLIPR buffer per sample well.

Assay of test compound effect on activation of the alpha7 nicotinic receptor channel is done by measurement of cytosolic $[Ca^{2+}]$ elevation as reported by increased FLUO-3 fluorescence using a two addition experimental design and FLIPR™ (Molecular Devices). Following a 30 second baseline recording, test compounds are added online (dilution scheme below) and cell response is recorded for an additional 5 minutes. After a second addition of ACh (30 μM, FAC), plates are read for an additional 4 minutes.

Test Compound Preparation

Multiple concentrations of test compounds are examined in parallel on each 96 well assay plate. In order to achieve 100 μM (1.00E-4 M) for the highest FAC of test compound, 24 μl of 10 mM test compound stock solution (100% DMSO) is added directly to 576 μl of FLIPR buffer (i.e. highest [test compound]=0.4 mM=4-fold FAC). Starting with the 0.4 mM test compound sample, test compounds are then diluted serially in FLIPR buffer (using Biomek 2000) resulting in the following test compound FACs:vehicle, 1.00E-4 M, 3.16E-5, 1.00E-5 M, 3.16E-6, 1.00E-6 M, 3.16E-7, 1.00E-7 M. Maximum FAC for DMSO=1% in the sample wells exposed to the highest FAC of test compound of 100 μM. Negative controls were madeby vehicle addition, followed by ACh addition. Positive controls were made by 1 μM PNU-120596 addition, followed by ACh addition.

Compound Activity

Values for $IC_{50}/EC_{50}$, intrinsic agonist activity and positive allosteric modulation for alpha 7 nAChR were determined using ACTIVITYBASE™ data analysis software. For dose-response data, either the fitted mid-point of the curve (inflection) or the point at which the curve crosses a threshold activity value (typically 50% of control) may be used to determine $IC_{50}/EC_{50}$.

Using the above assay, the compounds of the invention were determined to be positive allosteric modulators for alpha 7 nAChR. For example, the compound 5-Chloro-N-[(1S,3R)-2,2-dimethyl-3-(4-sulfamoyl-phenyl)-cyclopropyl]-2-methoxy-benzamide showed an $EC_{50}$ of 0.89, and intrinsic activity of 493.6, and positive allosteric modulation of 469.6.

Example 10

In Vivo Assay for Asthma and Lung Function

BALb/cJ mice are immunized with a standard immunization protocol. Briefly, mice (N=8/group) are immunized i.p. with ovalbumin (OVA; 10 μg) in alum on days 0 and 14. Mice are then challenged with aerosolized OVA (5%) on day 21 and 22. Animals receive vehicle (p.o.) or a compound of the invention (100 mg/kg p.o.) all starting on day 20.

Lung function is evaluated on day 23 using the Buxco system to measure PenH in response to an aerosol methacholine challenge. Mice are then euthanized and plasma samples collected at the end of the study.

Example 11

Formalin Pain Assay

Male Sprague Dawley rats (180-220 g) are placed in individual Plexiglas cylinders and allowed to acclimate to the testing environment for 30 min. Vehicle, drug or positive control (morphine 2 mg/kg) is administered subcutaneously at 5 ml/kg. 15 min post dosing, formalin (5% in 50 μl) is injected into plantar surface of the right hind paw using a 26-gauge needle. Rats are immediately put back to the observation chamber. Mirrors placed around the chamber allow unhindered observation of the formalin-injected paw. The duration of nociphensive behavior of each animal is recorded by a blinded observer using an automated behavioral timer. Hindpaw licking and shaking/lifting are recorded separately in 5 min bin, for a total of 60 min. The sum of time spent licking or shaking in seconds from time 0 to 5 min is considered the early phase, whereas the late phase is taken as the sum of seconds spent licking or shaking from 15 to 40 min. A plasma sample is collected.

Example 12

Colon Pain Assay

Adult male Sprague-Dawley rats (350-425 g; Harlan, Indianapolis, Ind.) are housed 1-2 per cage in an animal care facility. Rats are deeply anesthetized with pentobarbital sodium (45 mg/kg) administered intraperitoneally. Electrodes are placed and secured into the external oblique musculature for electromyographic (EMG) recording. Electrode leads are tunneled subcutaneously and exteriorized at the nape of the neck for future access. After surgery, rats are housed separately and allowed to recuperate for 4-5 days prior to testing.

The descending colon and rectum are distended by pressure-controlled inflation of a 7-8 cm-long flexible latex balloon tied around a flexible tube. The balloon is lubricated, inserted into the colon via the anus, and anchored by taping the balloon catheter to the base of the tail. Colorectal distension (CRD) is achieved by opening a solenoid gate to a constant pressure air reservoir. Intracolonic pressure is controlled and continuously monitored by a pressure control device. Response is quantified as the visceromotor response (VMR), a contraction of the abdominal and hindlimb musculature. EMG activity produced by contraction of the external oblique musculature is quantified using Spike2 software (Cambridge Electronic Design). Each distension trial lasts 60 sec, and EMG activity is quantified for 20 sec before distension (baseline), during 20 sec distension, and 20 sec after distention. The increase in total number of recorded counts during distension above baseline is defined as the response. Stable baseline responses to CRD (10, 20, 40 and 80 mmHg, 20 seconds, 4 minutes apart) are obtained in conscious, unsedated rats before any treatment.

Compounds are evaluated for effects on responses to colon distension initially in a model of acute visceral nociception and a model of colon hypersensitivity produced by intracolonic treatment with zymosan (1 mL, 25 mg/mL) instilled into the colon with a gavage needle inserted to a depth of about 6 cm. Experimental groups will consist of 8 rats each.

Acute visceral nociception: For testing effects of drug on acute visceral nociception, 1 of 3 doses of drug, vehicle or positive control (morphine, 2.5 mg/kg) are administered after baseline responses are established; responses to distension are followed over the next 60-90 minutes.

Visceral hypersensitivity: For testing effects of drug or vehicle after intracolonic treatment with zymosan, intracolonic treatment is given after baseline responses are established. Prior to drug testing at 4 hours, responses to distension are assessed to establish the presence of hypersensitivity. In zymosan-treated rats, administration of 1 of 3 doses of drug, vehicle or positive control (morphine, 2.5 mg/kg) are given 4 hours after zymosan treatment and responses to distension followed over the next 60-90 minutes.

Example 13

Cold Allodynia in Rats with a Chronic Constriction Injury of the Sciatic Nerve The effects of compounds of this invention on cold allodynia are determined using the chronic constriction injury (CCI) model of neuropathic pain in rats, where cold allodynia is measured in a cold-water bath with a metal-plate floor and water at a depth of 1.5-2.0 cm and a temperature of 3-4 °C. (Gogas, K. R. et al., Analgesia, 1997, 3, 1-8).

Specifically, CCI, rats are anesthetized; the trifurcation of the sciatic nerve is located and 4 ligatures (4-0, or 5-0 chromic gut) are placed circumferentially around the sciatic nerve proximal to the trifurcation. The rats are then allowed to recover from the surgery. On days 4-7 after surgery, the rats are initially assessed for cold-induced allodynia by individually placing the animals in the cold-water bath and recording the total lifts of the injured paw during a 1-min period of time: The injured paw is lifted out of the water. Paw lifts associated with locomotion or body repositioning are not recorded. Rats that displayed 5 lifts per min or more on day 4-7 following surgery are considered to exhibit cold allodynia and are used in subsequent studies. In the acute studies, vehicle, reference compound or compounds of this invention are administered subcutaneously (s.c.) 30 min before testing. The effects of repeated administration of the compounds of this invention on cold allodynia are determined 14, 20 or 38 h following the last oral dose of the following regimen: oral (p.o.) administration of vehicle, reference or a compound of this invention at ~12 h intervals (BID) for 7 days.

Example 14

Cognition Enhancement

The cognition-enhancing properties of compounds of the invention may be in a model of animal cognition: the novel object recognition task model. 4-Month-old male Wistar rats (Charles River, The Netherlands) were used. Compounds were prepared daily and dissolved in physiological saline and tested at three doses. Administration was always given i.p.

What is claimed is:

1. A compound of formula I:

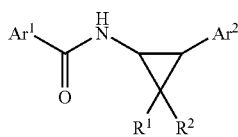

or a pharmaceutically acceptable salt thereof,
wherein:
Ar¹ is phenyl optionally substituted with one, two or three groups each selected independently from halo, halo-$C_{1-6}$alkyl, $C_{1-6}$alkyl and $C_{1-6}$alkoxy;
Ar² is phenyl optionally substituted once at the 4-position with halo, $C_{1-6}$alkyl, cyano, halo-$C_{1-6}$alkyl, $C_{1-6}$alkoxy or —(CR$^a$R$^b$)$_m$—X—R³ wherein:
m is 0;
X is —SO$_2$— or —C(O)—;
R³ is $C_{1-6}$alkyl or —NR⁴R⁵, and
R⁴ and R⁵ each independently is: hydrogen; or $C_{1-6}$alkyl;
R¹ and R² are $C_{1-6}$alkyl.

2. The compound of claim 1, wherein Ar¹ is 5-chloro-2-methoxy-phenyl, 5-chloro-2,4dimethoxy-phenyl, phenyl, 4-methyl-phenyl, 2-methoxy-5-methyl-phenyl, 2-methyl-5-methoxy-phenyl, 4-methoxy-2-methyl-phenyl, 2,5-dimethoxy-phenyl, 4-methoxy-phenyl, 4-chloro-phenyl, 3,4-dichloro-phenyl, 3-chloro-phenyl, 2-methoxy-phenyl, 4-tert-butyl-phenyl, 2,4-dimethoxy-phenyl, 3-trifluoromethyl-phenyl, 4-methanesulfonyl-phenyl, 4-aminosulfonyl-phenyl, 4-trifluoromethyl-phenyl, 5-fluoro-2-methoxy-phenyl, 2-methoxy-5-trifluoromethyl-phenyl, 2-methoxy-5-tert-butyl-phenyl, 4-chloro-2-methoxy-phenyl, 2,4,5-trimethoxy-phenyl, 2,6-dimethoxy-phenyl, or 2,3-dimethoxy-phenyl.

3. The compound of claim 1, wherein Ar² is phenyl substituted at the 4-position with cyano, —SO$_2$NH$_2$ or —SO$_2$—CH$_3$.

4. The compound of claim 1, wherein Ar² is phenyl, 4-aminosulfonyl-phenyl, 4-methylaminosulfonyl-phenyl, 4-dimethylaminosulfonyl-phenyl, 4-trifluoromethyl-phenyl, 4-methyl-phenyl, 4-chloro-phenyl, 4-methanesulfonyl-phenyl, 4-methoxy-phenyl, 4-cyano-phenyl or 4-bromo-phenyl.

5. The compound of claim 1, wherein R¹ and R² are methyl.

6. The compound of claim 1, wherein said compound of formula II:

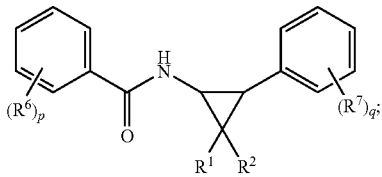

wherein:
p and q each independently is from 0 to 3;
R¹ and R² are methyl; and
R⁶ and R⁷ each independently is:
$C_{1-6}$alkyl;
halo;
$C_{1-6}$alkoxy;
halo-$C_{1-6}$alkoxy;
halo-$C_{1-6}$alkyl;
hetero-$C_{1-6}$alkyl;
cyano;
$C_{1-6}$alkyl-amino;
di-$C_{1-6}$alkyl-amino;
nitro; and
—(CR$^a$R$^b$)$_m$—X—R³ wherein:
m is 0;
X is —SO$_2$—,
R³ is $C_{1-6}$alkyl or —NR⁴R⁵, and
R⁴ and R⁵ each independently is:
hydrogen; or
$C_{1-6}$alkyl.

7. The compound of claim 6, wherein p is from 1 to 3 and each R⁶ is independently:
$C_{1-6}$alkyl;
halo;
$C_{1-6}$alkoxy;
halo-$C_{1-6}$alkoxy; or
halo-$C_{1-6}$alkyl.

8. The compound of claim 7, wherein q is 1 and R⁷ is $C_{1-6}$alkyl, halo-$C_{1-6}$alkyl or —(CR$^a$R$^b$)$_m$—X—R³ wherein:
m is 0;
X is —SO$_2$—;
R³ is $C_{1-6}$alkyl or —NR⁴R⁵, and
R⁴ and R⁵ each independently is:
hydrogen; or
$C_{1-6}$alkyl.

9. The compound of claim 8 wherein p is from 1 to 3 and R⁶ is halo or methoxy.

10. The compound of claim 9 wherein q is 1 and R⁷ is —SO$_2$NR⁴R⁵.

11. The compound of claim 1, wherein said compound of formula III:

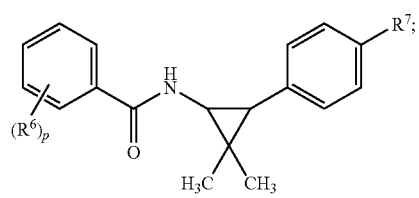

wherein:
p is from 0 to 3;
each $R^6$ is independently selected from:
$C_{1-6}$alkyl;
halo;
$C_{1-6}$alkoxy;
halo-$C_{1-6}$alkoxy; or
halo-$C_{1-6}$alkyl; and
$R^7$ is —$(CR^aR^b)_m$—X—$R^3$ wherein:
m is 0;
X is —$SO_2$—;
$R^3$ $C_{1-6}$alkyl or —$NR^4R^5$, and
$R^4$ and $R^5$ each independently is:
hydrogen; or
$C_{1-6}$alkyl.

12. The compound of claim 11, wherein p is from 1 to 3 and each $R^3$ is independently halo or methoxy.

13. The compound of claim 12, wherein $R^7$ is —$SO_2NR^4R^5$.

14. The compound of claim 13, wherein $R^4$ and $R^5$ each independently is hydrogen or methyl.

15. The compound of claim 1, wherein said compound of formula IIIa or IIIb:

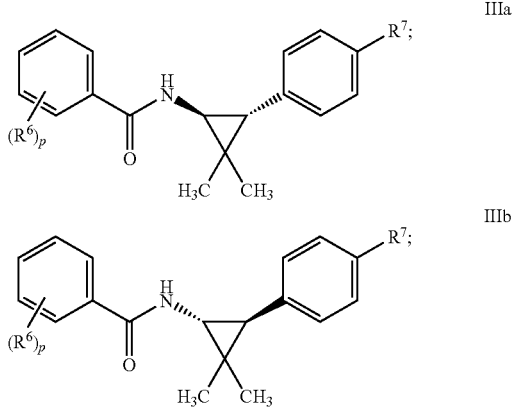

wherein p, $R^6$ and $R^7$ are as recited in claim 1.

16. A pharmaceutical composition comprising a compound of claim 1 and a pharmaceutically acceptable carrier.

17. A method for enhancing cognition in subject, said method comprising administering to said subject an effective amount of a compound of claim 1.

18. A compound selected from the group consisting of:
5-Chloro-N-[cis-2,2-dimethyl-3-(4-sulfamoyl-phenyl)-cyclopropyl]-2-methoxy-benzamide;
5-Chloro-N-[trans-2,2-dimethyl-3-(4-sulfamoyl-phenyl)-cyclopropyl]-2-methoxy-benzamide
5-Chloro-N-[(1R,3S)-2,2-dimethyl-3-(4-sulfamoyl-phenyl)-cyclopropyl]-2-methoxy-benzamide
5-Chloro-N-[(1S,3R)-2,2-dimethyl-3-(4-sulfamoyl-phenyl)-cyclopropyl]-2-methoxy-benzamide;
5-Chloro-N-[3-(4-dimethylsulfamoyl-phenyl)-trans-2,2-dimethyl-cyclopropyl]-2-methoxy-benzamide;
5-Chloro-N-[trans-2,2-dimethyl-3-(4-trifluoromethyl-phenyl)-cyclopropyl]-2-methoxy-benzamide;
5-Chloro-N-[trans-2,2-dimethyl-3-phenyl-cyclopropyl]-2-methoxy-benzamide;
5-Chloro-N-[trans-2,2-dimethyl-3-(4-trifluoromethyl-phenyl)-cyclopropyl]-2,4-dimethoxy-benzamide;
5-Chloro-N-[trans-2,2-dimethyl-3-p-tolyl-cyclopropyl]-2-methoxy-benzamide;
5-Chloro-N-[trans-2,2-dimethyl-3-p-tolyl-cyclopropyl]-2,4-dimethoxy-benzamide;
5-Chloro-N-[3-(4-chloro-phenyl)-trans-2,2-dimethyl-cyclopropyl]-2,4-dimethoxy-benzamide;
5-Chloro-N-[3-(4-chloro-phenyl)-trans-2,2-dimethyl-cyclopropyl]-2-methoxy-benzamide;
5-Chloro-N-[3-(4-methanesulfonyl-phenyl)-trans-2,2-dimethyl-cyclopropyl]-2-methoxy-benzamide;
5-Chloro-N-[trans-2,2-dimethyl-3-phenyl-cyclopropyl]-2,4-dimethoxy-benzamide;
N-[trans-2,2-Dimethyl-3-p-tolyl-cyclopropyl]-benzamide;
N-[trans-2,2-Dimethyl-3-p-tolyl-cyclopropyl]-4-methyl-benzamide;
N-[trans-2,2-Dimethyl-3-p-tolyl-cyclopropyl]-2-methoxy-5-methyl-benzamide;
N-[trans-2,2-Dimethyl-3-p-tolyl-cyclopropyl]-4-methoxy-2-methyl-benzamide;
N-[trans-2,2-Dimethyl-3-p-tolyl-cyclopropyl]-2,5-dimethoxy-benzamide;
N-[trans-2,2-Dimethyl-3-p-tolyl-cyclopropyl]-4-methoxy-benzamide;
4-Chloro-N-[trans-2,2-dimethyl-3-p-tolyl-cyclopropyl]-benzamide;
3,4-Dichloro-N-[trans-2,2-dimethyl-3-p-tolyl-cyclopropyl]-benzamide;
N-[3-(4-Chloro-phenyl)-trans-2,2-dimethyl-cyclopropyl]-2-methoxy-5-methyl-benzamide;
N-[3-(4-Chloro-phenyl)-trans-2,2-dimethyl-cyclopropyl]-4-methoxy-2-methyl-benzamide;
5-Chloro-2,4-dimethoxy-N-[3-(4-methoxy-phenyl)-trans-2,2-dimethyl-cyclopropyl]-benzamide;
5-Chloro-2-methoxy-N-[3-(4-methoxy-phenyl)-trans-2,2-dimethyl-cyclopropyl]-benzamide;
2-Methoxy-N-[3-(4-methoxy-phenyl)-trans-2,2-dimethyl-cyclopropyl]-5-methyl-benzamide;
4-Methoxy-N-[3-(4-methoxy-phenyl)-trans-2,2-dimethyl-cyclopropyl]-2-methyl-benzamide;
2,5-Dimethoxy-N-[3-(4-methoxy-phenyl)-trans-2,2-dimethyl-cyclopropyl]-benzamide;
N-[3-(4-Chloro-phenyl)-trans-2,2-dimethyl-cyclopropyl]-4-methyl-benzamide;
N-[3-(4-Chloro-phenyl)-trans-2,2-dimethyl-cyclopropyl]-benzamide;
3,4-Dichloro-N-[3-4-chloro-phenyl)-trans-2,2-dimethyl-cyclopropyl]-benzamide;
4-Chloro-N-[3-(4-chloro-phenyl)-trans-2,2-dimethyl-cyclopropyl]-benzamide;
N-[3-(4-Chloro-phenyl)-trans-2,2-dimethyl-cyclopropyl]-4-methoxy-benzamide;
N-[3-(4-methoxy-phenyl)-trans-2,2-dimethyl-cyclopropyl]-4-methyl-benzamide;
N-[3-(4-methoxy-phenyl)-trans-2,2-dimethyl-cyclopropyl]-benzamide;
3,4-Dichloro-N-[3-(4-methoxy-phenyl)-trans-2,2-dimethyl-cyclopropyl]-benzamide;
4-Chloro-N-[3-(4-methoxy-phenyl)-trans-2,2-dimethyl-cyclopropyl]-benzamide;
4-Methoxy-N-[3-(4-methoxy-phenyl)-trans-2,2-dimethyl-cyclopropyl]-benzamide;
5-Chloro-N-[(1S,3R)-2,2-dimethyl-3-(4-methylsulfamoyl-phenyl)-cyclopropyl]-2-methoxy-benzamide;
5-Chloro-N-[(1S,3R-2,2-dimethyl-3-(4-sulfamoyl-phenyl)-cyclopropyl]-2,4-dimethoxy-benzamide;
5-Chloro-N-[(1S,3R)-2,2-dimethyl-3-(4-methylsulfamoyl-phenyl)-cyclopropyl]-2,4-dimethoxy-benzamide;

5-Chloro-N-[3-(4-methanesulfonyl-phenyl)-(1S,3R)-2,2-dimethyl-cyclopropyl]-2-methoxy-benzamide;
5-Chloro-N-[trans-2,2-dimethyl-3-(4-sulfamoyl-phenyl)-cyclopropyl]-2,4-dimethoxy-benzamide;
N-[Trans-2,2-Dimethyl-3-(4-sulfamoyl-phenyl)-cyclopropyl]-4-methyl-benzamide;
N-[trans-2,2-Dimethyl-3-(4-sulfamoyl-phenyl)-cyclopropyl]-benzamide;
4-Chloro-N-[trans-2,2-dimethyl-3-(4-sulfamoyl-phenyl)-cyclopropyl]-benzamide;
N-[Trans-2,2-Dimethyl-3-(4-sulfamoyl-phenyl)cyclopropyl]-4-methoxy-benzamide;
3-Chloro-N-[trans-2,2-dimethyl-3-(4-sulfamoyl-phenyl)-cyclopropyl]-benzamide;
N-[trans-2,2-Dimethyl-3-(4-sulfamoyl-phenyl)-cyclopropyl]-2-methoxy-benzamide;
4-tert-Butyl-N-[trans-2,2-dimethyl-3-(4-sulfamoyl-phenyl)-cyclopropyl]-benzamide;
N-[Trans-2,2-Dimethyl-3-(4-sulfamoyl-phenyl)-cyclopropyl]-4-methoxy-2-methyl-benzamide;
N-[Trans-2,2-Dimethyl-3-(4-sulfamoyl-phenyl)-cyclopropyl]-2,4-dimethoxy-benzamide;
N-[Trans-2,2Dimethyl-3-(4-sulfamoyl-phenyl)-cyclopropyl]-3-trifluoromethyl benzamide;
3,4-Dichloro-N-[trans-2,2-dimethyl-3-(4-sulfamoyl-phenyl)-cyclopropyl]-benzamide;
5-Chloro-2-methoxy-N-[trans-2-phenyl)-cyclopropyl]-benzamide;
5-Chloro-2,4-methoxy-N-(trans-2-phenyl-cyclopropyl)-benzamide;
N-(Trans-2-2-Dimethyl-3-phenyl-cyclopropyl)-4-methanesulfonyl-benzamide;
N-(Trans-2,2-Dimethyl-3-phenyl-cyclopropyl)-4-sulfamoyl-benzamide;
5-Chloro-2,4-dimethoxy-N-[trans-2-(4-sulfamoyl-phenyl)-cyclopropyl]-benzamide;
5-Chloro-2-methoxy-N-[trans-2-(4-sulfamoyl-phenyl)-cyclopropyl]-benzamide;
N-[Trans-2,2-Dimethyl-3-(4-sulfamoyl-phenyl)-cyclopropyl]-4-trifluoromethyl-benzamide;
N-[Trans-2,2-Dimethyl-3-(4-sulfamoyl-phenyl)-cyclopropyl]-2,5-dimethoxy-benzamide;
5-Chloro-2-methoxy-N-[trans-2-methyl-3-(4-sulfamoyl-phenyl)-cyclopropyl]-benzamide;
5-Chloro-N-[Trans-7-ethyl-3-(4-sulfamoyl-phenyl)-cyclopropyl]-2-methoxy-benzamide;
N-[Trans-2,2-Dimethyl-3-(4-sulfamoyl-phenyl)-cyclopropyl]-5-fluoro-2-methoxy-benzamide;
N-[Trans-2,2-Dimethyl-3-(4-sulfamoyl-phenyl)-cyclopropyl]-5-methoxy-2-methyl-benzamide;
N-[Trans-2,2-Dimethyl-3-(4-sulfamoyl-phenyl)-cyclopropyl]-2,3,5-trimethoxy-benzamide;
N-[(1S,3R)-2,2-Dimethyl-3-(4sulfamoyl-phenyl)-cyclopropyl]-2,4-dimethoxy-benzamide;
N[Trans-2,2-Dimethyl-3-(4-sulfamoyl-phenyl)-cyclopropyl]-2-methoxy-5-trifluoromethyl-benzamide;
5-tert-Butyl-N-[trans-2,2-dimethyl-3-(4-sulfamoyl-phenyl)-cyclopropyl]-2-methoxy-benzamide;
N-[Trans-2,2-Dimethyl-3-(4-sulfamoyl-phenyl)-cyclopropyl]-2,4-dimethoxy-5-methyl-benzamide;
N-[Trans-2,2-Dimethyl-3-(4-sulfamoyl-phenyl)-cyclopropyl]-2-methoxy-4-methyl-benzamide;
N-[(1S,3R)-2,2-Dimethyl-3-(4-sulfamoyl-phenyl)-cyclopropyl]-5-fluoro-2-methoxy-benzamide;
5-Chloro-2-methoxy-N-[trans-3-(3-methoxy-4-sulfamoyl-phenyl)-2,2-dimethyl-cyclopropyl]-benzamide;
5-Chloro-N-[trans-3-(4-cyano-phenyl)-2,2-dimethyl-cyclopropyl]-2-methoxy-benzamide;
N-[Trans-3-(4-Bromo-phenyl)-2,2-dimethyl-cyclopropyl]-5-chloro-2-methoxy-benzamide;
4-Chloro-N-[trans-2,2-dimethyl-3-(4-sulfamoyl-phenyl)-cyclopropyl]-2-methoxy-benzamide;
5-Chloro-N-[trans-3-(4-methanesulfonyl-phenyl)-2,2-dimethyl-cyclopropyl]-2,4-dimethoxy-benzamide;
N-[Trans-2,2-Dimethyl-3-(4-sulfamoyl-phenyl)-cyclopropyl]-2,4,5-trimethoxy-benzamide;
N-[Trans-2,2-Dimethyl-3-(4-sulfamoyl-phenyl)-cyclopropyl]-2,6-dimethoxy-benzamide;
N-[Trans-3-(4-(4-Methanesulfonyl-phenyl)-2,2-dimethyl-cyclopropyl]-2,4-dimethoxy-benzamide;
N-[Trans-2,2-Dimethyl-3-(4-sulfamoyl-phenyl)-cyclopropyl]-2,3-dimethoxy-benzamide;
N-[Trans-2,2-Dimethyl-3-(4-sulfamoyl-phenyl)-cyclopropyl]-3-trifluoromethyl-benzamide;
2'-Methoxy-biphenyl-3-carboxylic acid[trans-2,2-dimethyl-3-(4-sulfamoyl-phenyl)-cyclopropyl]-amide;
5-Chloro-2-methoxy-N-[trans-3-(3-methoxy-phenyl)-2,2-dimethyl-cyclopropyl]-benzamide;
N-[Trans-2,2-Dimethyl-3-(3-trifluoromethyl-phenyl)-cyclopropyl]-4-methanesulfonyl-benzamide; and.

* * * * *